(12) United States Patent
DiMagno et al.

(10) Patent No.: US 9,903,858 B2
(45) Date of Patent: Feb. 27, 2018

(54) MULTIPLEXING WITH SINGLE SAMPLE METERING EVENT TO INCREASE THROUGHPUT

(71) Applicant: Ortho-Clinical Diagnostics, Inc., Raritan, NJ (US)

(72) Inventors: Theodore J. DiMagno, Penfield, NY (US); Joseph J. Dambra, Rochester, NY (US); Randy K. Bower, Pittsford, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 110 days.

(21) Appl. No.: 14/805,712

(22) Filed: Jul. 22, 2015

(65) Prior Publication Data
US 2016/0025715 A1 Jan. 28, 2016

Related U.S. Application Data

(60) Provisional application No. 62/027,843, filed on Jul. 23, 2014.

(51) Int. Cl.
*G01N 21/75* (2006.01)
*G01N 33/53* (2006.01)
(Continued)

(52) U.S. Cl.
CPC .... *G01N 33/5302* (2013.01); *B01L 3/502715* (2013.01); *G01N 27/3272* (2013.01);
(Continued)

(58) Field of Classification Search
CPC ........... G01N 33/5302; G01N 27/3272; G01N 2035/1032; B01L 3/502715;
(Continued)

(56) References Cited

U.S. PATENT DOCUMENTS 3,992,158 A 11/1976 Przybylowicz et al.
4,184,936 A 1/1980 Paul et al.
(Continued)

FOREIGN PATENT DOCUMENTS

EP 0 097 952 A2 1/1984
EP 2 120 048 A1 11/2009
(Continued)

OTHER PUBLICATIONS

International Search Report and Written Opinion for PCT/US2015/041700; dated Jan. 4, 2016; 15 pages.

*Primary Examiner* — Dennis White
(74) *Attorney, Agent, or Firm* — Barclay Damon, LLP

(57) ABSTRACT

An assay device includes a support, test elements arranged thereover, and a diverter defining a common sample addition area of the device. The diverter conducts respective portions of a fluidic sample from the area to each of the test elements. Another assay device includes the test elements, one a dry slide element, disposed over the support at least partly in proximity to each other to define a common sample addition area. Apparatus for analyzing a sample includes an assay device having the test elements, one a dry slide element. A controller operates a metering mechanism, to apply the sample to the assay device, an incubator, and a measurement device per a timing protocol to determine a characteristic of the sample. Methods for enabling an assay device to perform multiple tests based upon a single sample metering event include are also described.

18 Claims, 12 Drawing Sheets

(51) Int. Cl.
*G01N 27/327* (2006.01)
*B01L 3/00* (2006.01)
*G01N 35/10* (2006.01)

(52) U.S. Cl.
CPC . *B01L 2200/027* (2013.01); *B01L 2300/0816* (2013.01); *B01L 2300/0864* (2013.01); *B01L 2400/0406* (2013.01); *B01L 2400/0457* (2013.01); *G01N 2035/1032* (2013.01)

(58) Field of Classification Search
CPC ..... B01L 2400/0457; B01L 2300/0816; B01L 2300/0864; B01L 2400/0406; B01L 2200/027
See application file for complete search history.

(56) References Cited

U.S. PATENT DOCUMENTS

| | | | |
|---|---|---|---|
| 4,214,968 A | 7/1980 | Battaglia et al. | |
| 4,270,920 A | 6/1981 | Kondo et al. | |
| 4,287,155 A | 9/1981 | Tersteeg et al. | |
| 5,120,643 A | 6/1992 | Ching et al. | |
| 5,559,041 A | 9/1996 | Kang et al. | |
| 5,714,389 A | 2/1998 | Charlton et al. | |
| 5,981,298 A | 11/1999 | Chudzik et al. | |
| 6,139,800 A | 10/2000 | Chandler | |
| 6,228,660 B1 | 5/2001 | May et al. | |
| 6,251,083 B1 | 6/2001 | Yum et al. | |
| 6,544,796 B1 | 4/2003 | Eichenlaub et al. | |
| 7,052,831 B2 | 5/2006 | Fletcher et al. | |
| 7,312,084 B2 | 12/2007 | Jakubowicz et al. | |
| 7,416,700 B2 | 8/2008 | Buechler et al. | |
| 7,632,468 B2 | 12/2009 | Barski et al. | |
| 7,816,090 B2 | 10/2010 | Jacobs | |
| 8,025,854 B2 | 9/2011 | Ohman et al. | |
| 8,043,562 B2 | 10/2011 | Tomasso et al. | |
| 2004/0072367 A1 | 4/2004 | Ding et al. | |
| 2006/0134707 A1 | 6/2006 | Pellegrini et al. | |
| 2006/0285996 A1* | 12/2006 | Ohman | B01L 3/5023 422/400 |
| 2006/0289787 A1 | 12/2006 | Ohman et al. | |
| 2007/0231883 A1 | 10/2007 | Lindstrom et al. | |
| 2013/0280698 A1* | 10/2013 | Propper | G01N 33/5302 435/5 |

FOREIGN PATENT DOCUMENTS

| | | |
|---|---|---|
| WO | WO 03/103835 A1 | 12/2003 |
| WO | WO 2005/089082 A2 | 9/2005 |
| WO | WO 2005/108991 A2 | 11/2005 |
| WO | WO 2005/118139 A1 | 12/2005 |
| WO | WO 2006/137785 A1 | 12/2006 |

* cited by examiner

MULTIPLEXING WITH SINGLE SAMPLE METERING EVENT TO INCREASE THROUGHPUT

CROSS REFERENCE TO RELATED APPLICATIONS

This application claims priority pursuant to relevant portions of 35 U.S.C. § 119 to U.S. Patent Application No. 62/027,843, filed Jul. 23, 2014 and entitled: MULTIPLEXING WITH SINGLE SAMPLE METERING EVENT TO INCREASE THROUGHPUT, the entire contents of which are herein incorporated by reference.

TECHNICAL FIELD

This application relates to the field of clinical diagnostics and more specifically to use of an assay device to detect analytes in clinical samples.

BACKGROUND

The use of diagnostic assays is very well known for the diagnosis, treatment and management of many diseases. In that regard, different types of diagnostic assays have been developed to simplify the detection of various analytes in clinical samples such as blood, serum, plasma, urine, saliva, tissue biopsies, stool, sputum, skin or throat swabs and tissue samples or processed tissue samples. These assays are frequently expected to provide a fast and reliable result, while being easy to use and inexpensive to manufacture.

One common type of disposable assay device is a "dry slide" such as those described in U.S. Pat. No. 3,992,158 to Przybylowicz, et al., issued Nov. 16, 1976. This document describes an integral analytical element, the dry slide, having a sample-spreading layer in fluid contact with a superposed reagent layer. The reagent layer contains a material interactive with an analyte or a precursor of a reaction product of an analyte, and within which a detectable change in optical or electronic properties of the reagent layer can be produced by virtue of such interactive material. Such a change, which can be the generation or destruction of coloration or fluorescence, can be detected quantitatively by radiometric techniques and, if desired, by automatic radiometric sensing devices such as photometric devices. Modern diagnostic analyzers provided automated handling of dry slides and automated measurement of samples using the dry slides. This permits testing a large number of samples in a relatively short period of time.

Specifically, there are generally two different types of slide elements, each relating to a form of patient sample testing that is required. A "potentiometric" slide element, such as described by U.S. Pat. No. 4,184,936 (Paul, et al.) and U.S. Pat. No. 4,214,968 (Battaglia, et al.), incorporated herein in their entirety, includes a pair of electrodes which can be interfaced with an electrometer or other suitable test apparatus capable of detecting an electrical property produced by a deposited test sample. A "colorimetric" slide element, on the other hand, is capable of being read by a reflectometer or other suitable apparatus capable of detecting an optical property, e.g., fluorescence, produced by or deposited onto the element through a read area provided on the test element which is aligned with an optical window of the testing device. Colorimetric slide elements are further categorized as to the type of testing required. Endpoint testing, for example, requires only a single optical read after a predetermined incubation interval, while rate chemistry tests require multiple optical reads during various points of an incubation cycle.

In the field of medical diagnostics, there is a continued need to improve throughput of analyzers, e.g., to permit their use in large-volume testing centers such as reference laboratories. Various prior schemes add parallel processes to the analyzers, e.g., additional incubators, additional metering systems, or additional readers. Other schemes multiplex assays by running multiple assays on a single analyzer or running multiple analyzers at the same time. However, these prior schemes increase the size and complexity of individual analyzers or laboratories using those analyzers. Moreover, increasing throughput according to prior schemes increases the use of the hardware and can accelerate the time to failure of any given component of an analyzer. There is, therefore, a need for ways of increasing assay throughput without the aforementioned disadvantages.

BRIEF DESCRIPTION

According to an aspect of the invention, there is provided an assay device comprising:
  a) a support;
  b) two or more test elements arranged at least partially over the support; and
  c) a diverter arranged in relation to the at least two test elements and the support, said diverter defining a common sample addition area of the device and configured to conduct respective portions of a fluidic sample from the sample addition area to each of the at least two test elements.

According to another aspect of the invention, there is provided an assay device comprising:
  a) a support; and
  b) at least two test elements disposed at least partially over the support at least partly in proximity to each other to define a common sample addition area, wherein at least one of the at least two test elements is a dry slide analytical test element.

According to yet another aspect of the invention, there is provided apparatus for analyzing a fluidic sample, the system comprising:
  a) at least one assay device comprising a support and at least two test elements, wherein at least one of the at least two test elements is a dry slide analytical test element;
  b) a metering mechanism configured to selectively apply the fluidic sample to the at least one assay device;
  c) at least one incubator;
  d) at least one measurement device; and
  e) a controller configured to operate each of the metering mechanism, incubator, and at least one measurement device in accordance with a predetermined timing protocol in order to determine at least one characteristic of the applied fluidic sample.

According to still another aspect of the invention, there is provided a method for enabling an assay device to perform multiple tests based upon a single sample metering event, the method comprising:
  providing a support of the assay device; and
  disposing at least two test elements at least partially over the support to define a common sample addition area, wherein at least one of the at least two test elements is a dry slide analytical test element;
  wherein the at least two test elements are configured to receive respective portions of a single fluidic sample metered from a fluid supply during the single sample metering event onto the common sample addition area.

Various embodiments advantageously increase test throughput without adding additional processes and actuations to the system. For example, typical blood panels include a Basic Metabolic Panel (7 tests), a Comprehensive Metabolic Panel (14 tests), and a Lipid Panel (4 tests). Using an assay device including seven test elements corresponding to the seven tests in a Basic Metabolic Panel advantageously provides a seven-fold increase in the rate at which Basic Metabolic Panels can be run. Similar increases in speed are possible for other panels and tests by selecting appropriate test elements for each assay device. This increase in speed is advantageously provided without significant increases in the physical space occupied by the analyzer, permitting a given laboratory to run more tests without substantial physical reconfiguration.

This brief description is intended only to provide a brief overview of subject matter disclosed herein according to one or more illustrative embodiments, and does not serve as a guide to interpreting the claims or to define or limit scope, which is defined only by the appended claims. This brief description is provided to introduce an illustrative selection of concepts in a simplified form that are further described below in the Detailed Description. This brief description is not intended to identify key features or essential features of the claimed subject matter, nor is it intended to be used as an aid in determining the scope of the claimed subject matter. The claimed subject matter is not limited to implementations that solve any or all disadvantages noted in the Background.

BRIEF DESCRIPTION OF THE DRAWINGS

The above and other objects, features, and advantages will become more apparent when taken in conjunction with the following description and drawings wherein identical reference numerals have been used, where possible, to designate identical features that are common to the figures, and wherein.

Figure 1A:
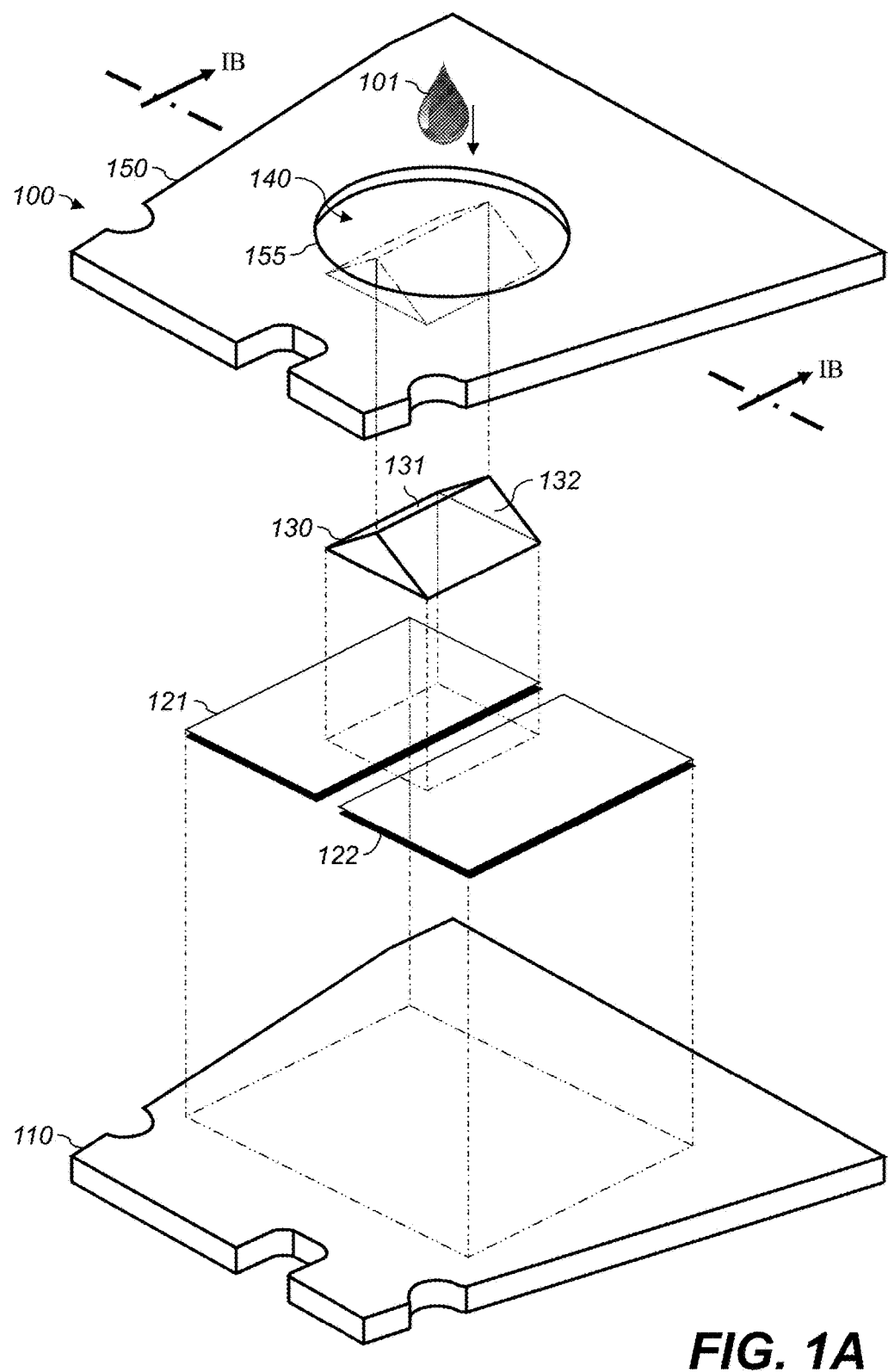
FIG. 1A is an exploded perspective view of an exemplary assay device in accordance with various embodiments.

The attached drawings are for purposes of illustration and are not necessarily presented to scale. Therefore, no narrowing interpretation should be made in terms of dimensions that have been depicted.

DETAILED DESCRIPTION

Throughout this description, some aspects are described in terms that would ordinarily be implemented as software programs. Those skilled in the art will readily recognize that the equivalent of such software can also be constructed in hardware, firmware, or micro-code. Because data-manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

The following description relates to certain embodiments for assay devices, analyzers, and related methods. It will be readily apparent that the embodiments described herein are intended to be exemplary and therefore numerous other variations and modifications are possible. In addition, several terms are used throughout the following discussion for purposes of providing a suitable frame of reference in regard to the accompanying drawings. To that end, these terms should not be regarded as being overly restrictive in terms of the scope of the described apparatus and methods, unless otherwise specifically indicated herein.

As used in this specification and the appended claims, the singular forms "a", "an" and "the" are intended to further include plural referents unless the context clearly dictates otherwise.

The term "about" as used in connection with a numerical value throughout the description and the claims denotes an interval of accuracy, familiar and acceptable to a person skilled in the art. The interval governing this term is preferably ±10%.

In terms of defining certain of the terms that follow, the term "analyte" is used as a synonym of the term "marker" and intended to minimally encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The term "sample" herein means a volume of a liquid, solution or suspension, intended to be subjected to qualitative or quantitative determination of any of its properties, such as the presence or absence of a component, the concentration of a component, etc. Typical samples in the context of the present disclosure are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments are applicable to all bodily samples, but preferably to samples of whole blood, serum, plasma, urine or sputum.

In other instances, the sample can be related to food testing, environmental testing, bio-threat or bio-hazard testing, etc. This represents only a small example of samples that can be used in various aspects.

In several versions, determination of an analyte is based on the interaction of components present in the sample with reagents present in the assay device or added to the assay device during a measurement procedure, and detection of such interaction, either quantitatively or qualitatively. Analyte determination may be for any purpose, such as diagnostic purposes. Some versions relate to assay devices using lateral-flow of a sample, often referred to as lateral-flow assays.

Examples of diagnostic determinations include, but are not limited to, the determination of analytes, also called markers, specific for different disorders, e.g., chronic metabolic disorders, such as blood glucose, blood ketones, urine glucose (diabetes), blood cholesterol (atherosclerosis, obesity, etc.); markers of other specific diseases, e.g., acute diseases, such as coronary infarct markers (e.g., troponin-T, NT-ProBNP), markers of thyroid function (e.g., determination of thyroid stimulating hormone (TSH)), markers of viral infections (the use of lateral-flow immunoassays for the detection of specific viral antibodies), etc.

Yet another important field is the field of companion diagnostics in which a therapeutic agent, such as a drug, is administered to an individual in need of such a drug. An appropriate assay is then conducted to determine the level of an appropriate marker to determine whether the drug is having its desired effect. Alternatively, the assay device usable with the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites in a urine or other sample.

The terms "automated clinical analyzer", "clinical diagnostic apparatus" or "clinical analyzer" as discussed herein, refer to any apparatus enabling the scheduling and processing of various analytical test elements, including lateral-flow assay devices, as discussed herein and in which a plurality of test elements can be initially loaded for processing. This apparatus further includes a plurality of components/systems configured for loading, incubating and testing/evaluating a plurality of analytical test elements in automated or semi-automated fashion and in which test elements are automatically dispensed from at least one contained storage supply, such as a cartridge, without user intervention.

The term "testing apparatus" refers to any device or analytical system that enables the support, scheduling and processing of lateral-flow assay devices. A testing apparatus can include an automated clinical analyzer or clinical diagnostic apparatus such as a bench, table-top or main frame clinical analyzer, as well as point of care and other suitable devices. For purposes of this definition, the testing apparatus may include a plurality of components/systems for loading and testing/evaluating of at least one assay device including detection instruments for detecting the presence of at least one detectable signal of the assay device.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

The term "detection" and "detection signal" refers herein to the ability to provide a perceivable indicator that can be monitored either visually and/or by machine vision such as a detection instrument.

Throughout the course of discussion, certain terms such as "inner", "outer", "lateral", "vertical", "horizontal", "upper", "lower", "over", "under", and the like are used to provide a frame of reference with regard to the accompanying drawings showing, e.g., assay devices 100, 200, 300, 500, 600, 700, 800, 1000, 1200. These terms, however, except as indicated otherwise, should not be construed as limiting with regard to the herein-described embodiments or orientations or configurations in which assay devices according to such embodiments can be used.

Referring to FIG. 1A, there is shown an exploded perspective of an exemplary assay device 100. Relationships between the parts when assembled are shown in phantom. The assay device 100 includes a support 110 that retains two or more test elements 121, 122 arranged at least partially over the support 110. The assay device 100 is configured for use with, e.g., a single metered sample 101 (represented graphically using a teardrop shape). The metered sample 101 can be, e.g., a fluidic sample 101 of blood, plasma, or another bodily fluid, human or animal; or a solution containing a compound to be tested in a research laboratory. An exemplary assay device 100 can be, e.g., ~2.54 cm×~2.54 cm (~1"×~1") in size.

The support 110 can be, e.g., rectangular or trapezoidal in shape. In the illustrated example, the support 110 is substantially trapezoidal in shape. One or more orientation notches or recesses can be provided in the support 110 for use by automated handling equipment in the analyzer. The support 110 can include a planar supporting substrate under two test elements 121, 122, as shown, or can include a bracket, adhesive layer or mass, or other structure holding the test elements 121, 122 together.

Each of the test elements 121, 122 can include a film coated with, or a porous material impregnated with, an analyte or chemical reagent, as is well known in the art. Common test slides used in biological fluid analysis include, for example, one for a calcium (Ca) test, another for an aspartate transaminase (AST) test, and a third for a glucose (Glu) test. Additional details of this and other configurations of assay devices 100 are described in U.S. Pat. No. 7,632,468 to Barski, et al., issued Dec. 15, 2009, incorporated herein by reference in its entirety. Specifically, in at least one exemplary embodiment, at least one of the two or more test elements 121, 122 is a dry slide analytical test element. A dry slide analytical test element can include a spreading layer configured to receive the respective portion of the single fluidic sample 101, and a reagent layer arranged facing the spreading layer and in fluid contact with the spreading layer. Dry slide test elements 121, 122 useful with various aspects are described, e.g., in U.S. Pat. No. 3,992,158 to Przybylowicz, et al., which is incorporated herein by reference in its entirety. In another example, each of the test elements 121, 122 can include a tensioned slit of filter paper. The diverter 130 can be arranged wholly or partially over the two slits. Adhesive or another bonding structure can hold the test elements 121, 122 in position with respect to each other and the diverter 130.

Conventional dry slide assay devices (not shown) generally include a base and a single chemically-active element (e.g., coated film). According to some embodiments, each test element 121, 122 can include only the chemically-active portion of a dry slide assay device, i.e., not the base thereof. In other embodiments, each test element 121, 122 can include the respective base and the chemically-active element. Any such base of or included in the test elements 121, 122 is present in addition to the support 110 of the assay device 100. In an example, each test element 121, 122 is approximately 0.279 mm (11 mil) thick, or approximately 0.432 mm (17 mil) thick. The assay device 100 as a whole can be, e.g., approximately 1.09 mm (43 mil) thick.

The assay device 100 also includes a diverter 130 arranged in relation to the at least two test elements 121, 122 and the support 110. The diverter 130 defines a common sample addition area 140 of the assay device 100. The diverter 130 is configured to conduct respective portions (not shown) of a fluidic metered sample 101 from the common sample addition area 140 to each of the at least two test elements 121, 122. In various embodiments and as shown, the diverter 130 is at least partly arranged over or contacting less than the entirety of each of the test elements 121, 122. In other embodiments, the diverter 130 is arranged over or contacts the entirety of at least one of the test elements 121, 122. In this example, the diverter 130 includes two faces 131, 132 corresponding to the respective test elements 121, 122. The faces 131, 132 are surfaces down which the respective portions of the fluidic sample 101 can flow.

In various aspects, the assay device 100 further includes a cover 150 having an aperture 155, e.g., an opening in the cover 150, operatively arranged with respect to the common sample addition area 140 to receive the fluidic sample 101. In these aspects, the at least two test elements 121, 122 and the diverter 130 are arranged between the support 110 and the cover 150, as shown.

Accordingly, the diverter 130 in this example splits the single metered sample 101 into two or more aliquots that are applied to or activate two or more test elements 121, 122 at substantially the same time.

The fluidic sample 101 is metered onto the assay device 100, and flow of the metered fluidic sample 101 is directed to the multiple test elements 121, 122 using the diverter 130, also referred to in various aspects as a "bridge." The exemplary cover 150 and aperture 155 are constructed in such a way that the fluidic sample 101 metered into the aperture 155 flows down the slopes of the sides of the exemplary diverter 130, which is configured as a triangular prism according to the illustrated embodiment, onto the test elements 121, 122.

Various embodiments described herein advantageously include the diverter 130 configured to spread the fluidic sample 101 across multiple test elements 121, 122 passively. That is, the diverter 130 is shaped so that the physical properties of the fluidic sample 101 will cause the fluidic sample 101 to be divided into the respective portions for the respective test elements 121, 122. In this way, with a single sample metering event, multiple tests or assays can be conducted. This advantageously decreases the number of physical metering events per number of assay results. This also advantageously permits more assay tests to begin within the timing cycle of an analyzer (e.g., an analyzer apparatus 1100, FIG. 11), permitting greater assay throughput per timing cycle of the analyzer. The decrease of analyzer actuations per test result advantageously improves both system throughput and system reliability.

Figure 1B:
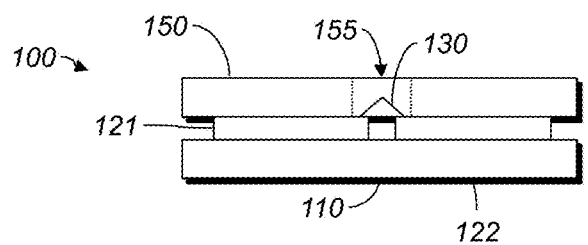
FIG. 1B is an elevational section through the line IB-IB in FIG. 1A.

Referring to FIG. 1B, there is shown an elevational section of the assay device 100 through the line IB-IB on FIG. 1A. As shown, in this example, the cover 150 is substantially co-planar with the diverter 130. The term "co-planar," as used herein, does not require that the cover 150 or the diverter 130 have any particular thickness. The term "co-planar" signifies that neither the cover 150 nor the diverter 130 extends substantially above or below the other. In the example shown, the diverter 130 fits into the aperture 155 in the cover 150. In other examples, the diverter 130 is formed together with the cover 150, e.g., by injection molding a single plastic piece including both the cover 150 and the diverter 130. An example of this is discussed below with reference to a diverter 630, FIG. 6.

Figure 2A:
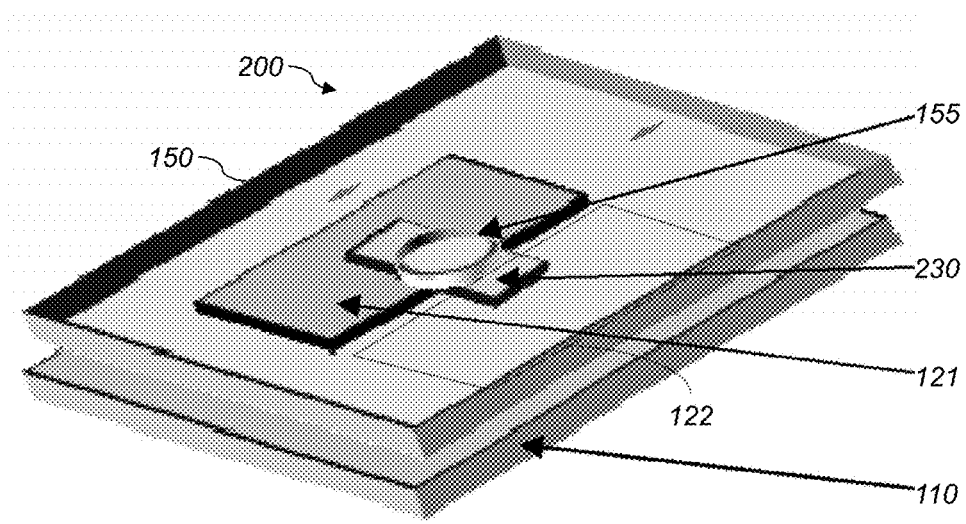
FIG. 2A is a perspective view.
Figure 2B:
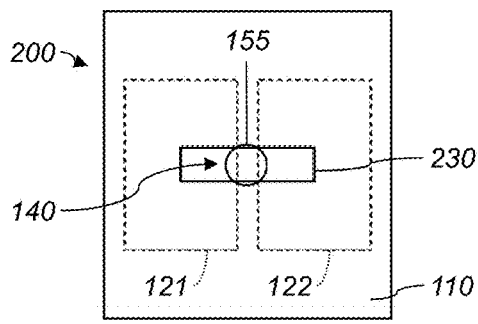
FIG. 2B is a plan view.
Figure 2C:
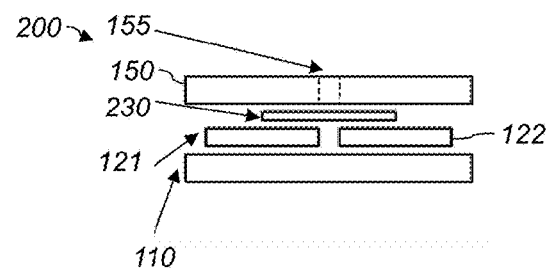
FIG. 2C is an elevational view of an exemplary assay device in accordance with various embodiments.

Referring to FIGS. 2A-2C, there is shown another configuration of an assay device 200 using a diverter. FIG. 2A is a perspective view, FIG. 2B is a plan view, and FIG. 2C is an elevational view. In this exemplary version, the diverter comprises a single porous member 230 arranged at least partly over each of the at least two test elements 121, 122. For example, the porous member 230 can include filter paper, cellulose, an open-cell foam, or a wicking material commonly used in a wicking zone 805, FIG. 8. At each interface between the porous member 230 and one of the at least two test elements 121, 122, the capillary force pulling the respective portion out of the porous member 230 is preferably stronger than the capillary force pushing the respective portion into the porous member 230.

The assay device 200 can also include the cover 150 with the aperture 155 over the porous member 230, and the support 110 under the test elements 121, 122. As shown in FIG. 2C, in this example, the cover 150 and the diverter (the porous member 230) are not co-planar. In at least one version for use, e.g., with whole blood samples, the porous member 230 has pores of sizes effective to separate red blood cells out of the whole blood fluidic sample 101, and an overall configuration effective to multiplex the fluidic sample 101 to the test elements 121, 122.

In an example of the use of assay device 200, the fluidic sample 101, FIG. 1, is metered on the center of the porous member 230, e.g., a piece of filter paper (or some comparable material). The fluidic sample 101 can be metered through the aperture 155, also referred to as a "sample drop hole," directly onto the porous member 230. The porous member 230 thus becomes saturated with the fluidic sample 101 and excess fluid of the fluidic sample 101 flows from the saturated porous member 230 to two or more test elements 121, 122 in contact with the porous member 230. An opening can be provided in the support 110 to permit measurement using reflectance (or any other suitable means such as absorption, fluorescence, or others known in the art, e.g., as discussed below with reference to the measurement device 1140, FIG. 11). Each test element 121, 122 receives a respective portion of the same fluidic sample 101 and can be independently measured to determine the concentration of a respective analyte in the fluidic sample 101. Using the assay device 200 thus permits two or more test elements 121, 122 to be metered with a single metering event, thus reducing the number of analyzer actuations and increasing throughput.

In at least one example, the porous member 230 is partly coated with a "blocking material," e.g., plastic or another material substantially impermeable to the fluidic sample 101. Alternatively, the blocking material can be arranged at least partly between the porous member 230 and one or more of the test elements 121, 122. In these examples, the blocking material controls the area in which the fluid of each respective portion transfers from the porous member 230 to the respective test element 121, 122. For example, a plastic coating on the underside of the porous member 230 can prevent or restrict fluid transfer so that fluid first enters the respective test element 121, 122 at a gap in the plastic coating (or other blocking material) at a defined location. Moreover, by providing respective, different sizes (e.g., areas) of gaps in the blocking material corresponding to respective ones of the test elements 121, 122, the relative volumes of the fluidic sample 101 transferred to each of the test elements 121, 122 can be adjusted. This advantageously permits combining, on a single assay device 200, multiple tests that would otherwise be incompatible as requiring, e.g., different amounts of fluid. Similarly, adjusting the size of the porous member 230 can provide these advantages. For example, by adjusting the blocking material or cross-sectional area of the porous member 230, test element 121 can be provided with 10 µL of the metered fluidic sample 101 via a first segment (not shown) of the porous member 230 having a first cross-sectional area with respect to the direction of fluid flow in the first segment, and test element 122 on the same assay device 200 can be provided with 5 µL of the metered fluidic sample 101 via a second segment (not shown) of the porous member 230 having a second, different cross-sectional area with respect to the direction of fluid flow in the second segment. The first and second segments can be formed, e.g., by molding the porous member 230 in a mold having the appropriate shape, or by cutting or trimming portions of a formed porous member 230.

Specifically, according to various aspects, the diverter 130 comprises a porous member 230 arranged at least partly over each of the at least two test elements 121, 122, the device further including a blocking material (not shown) substantially impermeable to the fluidic sample 101 and arranged at least partly between the porous member 230 and at least one of the two or more test elements 121, 122. In some of these aspects, the blocking material is arranged to define respective gaps (not shown) through which the respective portions of the fluidic sample 101 can pass from the diverter 130 to the respective ones of the two or more test elements 121, 1222, and at least two of the respective gaps have respective, different sizes. In other embodiments, the diverter 130 comprises a porous member 230 arranged at least partly over each of the at least two test elements 121, 122, the porous member 230 having a plurality of segments (not shown) corresponding to respective ones of the two or more test elements 121, 122 to carry fluid thereto, wherein at least two of the segments have respective, different cross-sectional areas.

Figure 3:
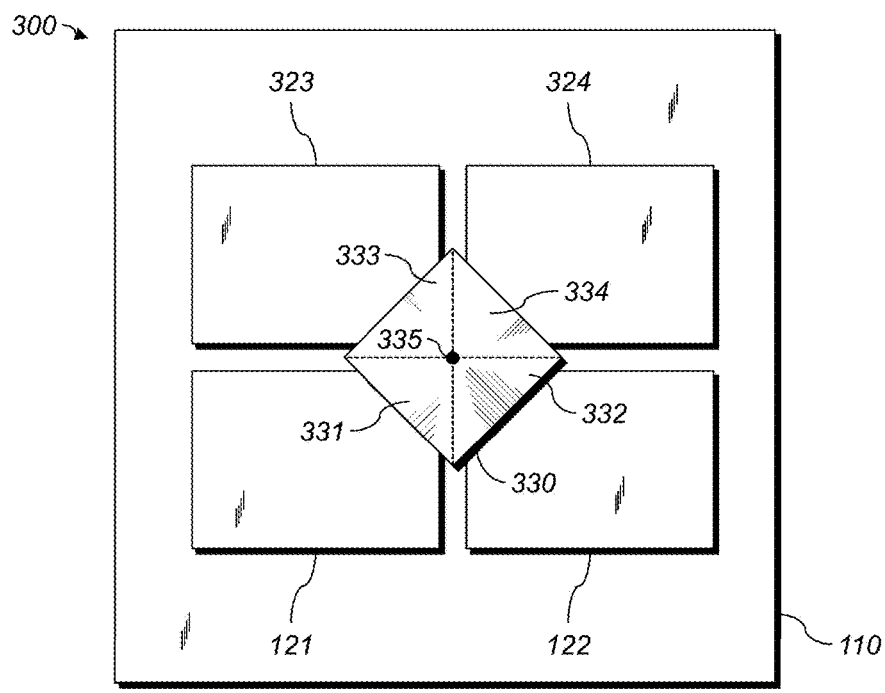
FIG. 3 is a plan view of an exemplary assay device in accordance with various embodiments.

Referring to FIG. 3, there is shown an exemplary assay device 300 having four test elements 121, 122, 323, and 324. A diverter 330 has a polyhedral configuration. In this example, the diverter 330 comprises a pyramid configured so that the applied fluidic sample 101 flowing along each face 331, 332, 333, 334 travels away from an apex 335 of the pyramid, e.g., towards a respective test element 121, 122, 323, 324. The pyramidal diverter 330 in this example has a square base and four edges leading between the corners of the base and the apex 335. The four edges are shown dashed for clarity. In this and other aspects, the diverter 330 includes a polyhedral configuration including a plurality of the faces 331, 332, 333, 334 disposed in relation to each of the at least two test elements 121, 122, 323, 324 and configured such that applied sample, e.g., the respective portion of the fluidic sample 101, flows along the respective face 331, 332, 333, 334 to a corresponding test element 121, 122, 323, 324. In several versions using the diverters 130, 330 over which the applied fluidic sample 101 flows, the diverter 130, 330 can consist of one or more material(s) that are substantially impermeable to the fluidic sample 101. For example, the diverter 330 can be injection-molded from plastic, e.g., polystyrene, to resist ingress of an aqueous fluidic sample 101, FIG. 1.

As described above with reference to FIG. 2, parameters of the diverter 330 can be designed to provide respective, different amounts of fluid to different ones of the test elements 121, 122, 323, 324, or to control the areas on the test elements 121, 122, 323, 324 first contacted by the respective portion of the metered sample 101. For pyramidal diverters 330 such as that illustrated, such parameters can include face size, face angle, number of faces, position of the apex 335 with respect to the base 410, FIG. 4, height, slope, material, and surface finish. This is also the case for the diverters 430, 530, and 630, described in FIGS. 4, 5, and 6, respectively.

Figures 4, 5:
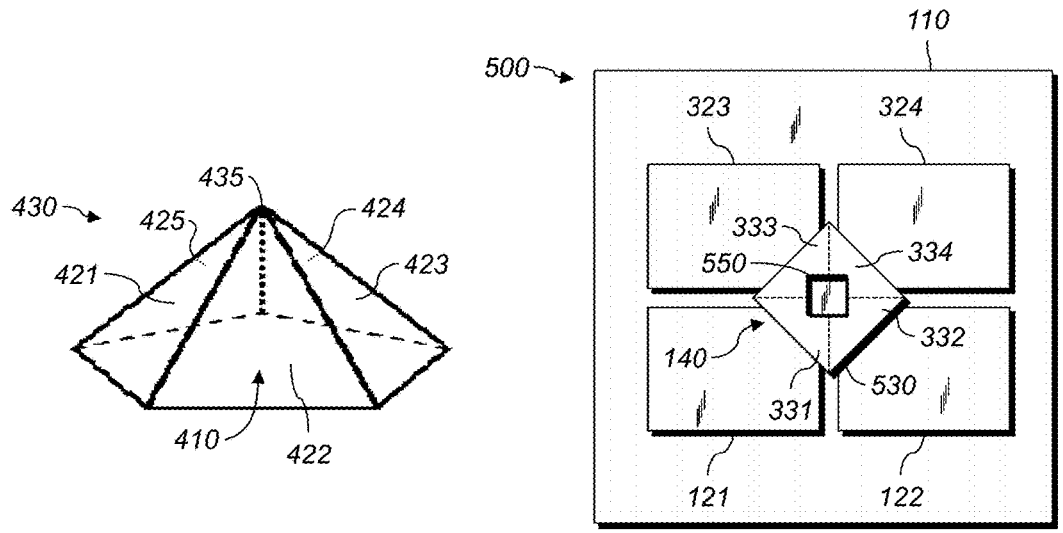
FIG. 4 is a perspective view of an exemplary pyramidal diverter in accordance with various embodiments.
FIG. 5 is a plan view of an exemplary assay device in accordance with various embodiments.

Referring to FIG. 4, there is shown an exemplary pyramidal diverter 430 according to an embodiment. The diverter 430 has a pentagonal base 410 and an apex 435. Between the base 410 and the apex 435 are arranged faces 421, 422, 423, 424, and 425.

In this and other examples, the diverter 430 or other diverters herein, e.g., the diverter 330, FIG. 3, and the test elements, e.g., the test elements 121, 122, 323, 324, FIG. 3, can be arranged in many different geometries to permit multiple test elements 121, 122, 323, 324 to be metered by, i.e., to receive portions (not shown) of a fluidic sample 101 from, a single sample metering event. For example, a pentagonal pyramid bridge such as the diverter 430 shown in FIG. 4 can simultaneously spot (apply a portion of the fluidic sample 101 to) five test elements (not shown) adjacent to each triangle face 421, 422, 423, 424, and 425 with a single metered fluidic sample 101.

Referring to FIG. 5, there is depicted another exemplary assay device 500. The assay device 500 is similar to the assay device 300, FIG. 3. The assay device 500 includes the four test elements 121, 122, 323, 324 and a pyramidal diverter 530. The assay device 500 also includes a fluid reservoir 550 located in the common sample addition area 140. The fluid reservoir 550 is configured to receive the fluidic sample 101, FIG. 1, and convey at least part of the fluidic sample 101 to the diverter 530. The fluid reservoir 550 can advantageously provided a buffer between a rapid-flow metering mechanism 1120 and ones of the test elements 121, 122, 323, 324 that require slower flow.

Figure 6:
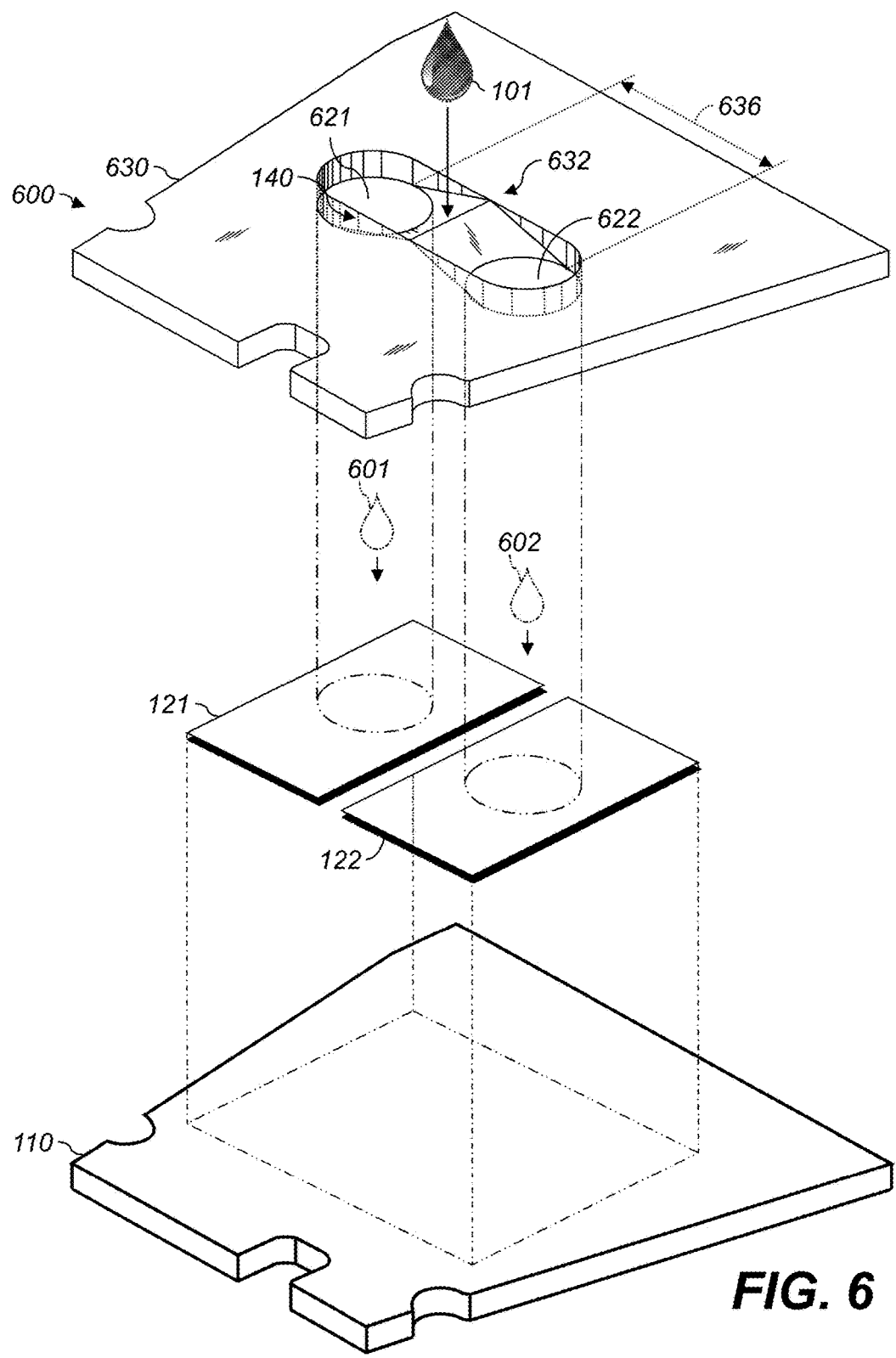
FIG. 6 is an exploded perspective view of an exemplary assay device in accordance with various embodiments.

Referring to FIG. 6, there is shown an exploded perspective of another exemplary assay device 600. Relationships between the parts when assembled are shown in phantom. The assay device 100 includes the support 110 that retains the two or more test elements 121, 122. A diverter 630 is arranged over the at least two test elements 121, 122. The diverter 630 includes a respective drop aperture 621, 622 for each of the at least two test elements 121, 122.

The diverter 630 also includes a splitter 632 configured to receive the fluidic sample 101 and provide the respective portions 601, 602 of the fluidic sample 101 to the respective drop apertures 621, 622. For clarity, the portions 601, 602 are graphically represented as drops after passing through the respective drop apertures 621, 622. The term "splitter" is not limited to the aspect shown, but can encompass other mechanical structures configured to passively divide a fluidic sample 101 metered onto the splitter 632 into two or more portions 601, 602.

In this example and according to various embodiments, the splitter 632 is sealed to the diverter 630 to constrain the metered fluidic sample 101 to travel only to the drop apertures 621, 622. In this and other examples, the drop apertures 621, 622 are laterally spaced apart from the edges of the test elements 121, 122. For example, as shown in FIG. 6, the drop apertures 621, 622 are roughly centered over the respective test elements 121, 122. This reduces the probability that the metered fluidic sample 101 will leak between the two test elements 121, 122.

In various aspects, the diverter 630 performs the functions of both the diverter 130 and the cover 150 (both FIG. 1A). The diverter 630 can be produced by, e.g., injection-molding a plastic or other material into the desired shape, including the splitter 632. The diverter 630 can alternatively be produced by machining a blank having the two drop apertures 621, 622 to form the splitter 632. For example, material can be ground or filed off the diverter 630, or otherwise removed from the diverter 630, to form the splitter 632. An example of a splitter 632 is discussed below with reference to FIGS. 15A-15B. In use, the splitter 632 is preferentially oriented so that gravity or another force acting on the fluidic sample 101 will draw the metered fluidic sample 101 across the splitter 632 to the drop apertures 621, 622. For example, the assay device 600 can be oriented splitter-side-up to use gravity.

In various examples, a distance 636 between the drop apertures 621, 622, e.g., between the centers of the drop apertures 621, 622 as shown, is selected to control where the metered portions 601, 602 first contact the respective test elements 121, 122. In at least one example, the respective edges of the drop apertures 621, 622 closest to the center of the diverter 630 receive the portions 601, 602 before other portions of the perimeters of the drop apertures 621, 622. Accordingly, these respective edges can be positioned substantially over the centers of the respective test elements 121, 122 so that the portions 601, 602 begin spotting the test elements 121, 122 from the centers of those test elements 121, 122.

Figure 7:
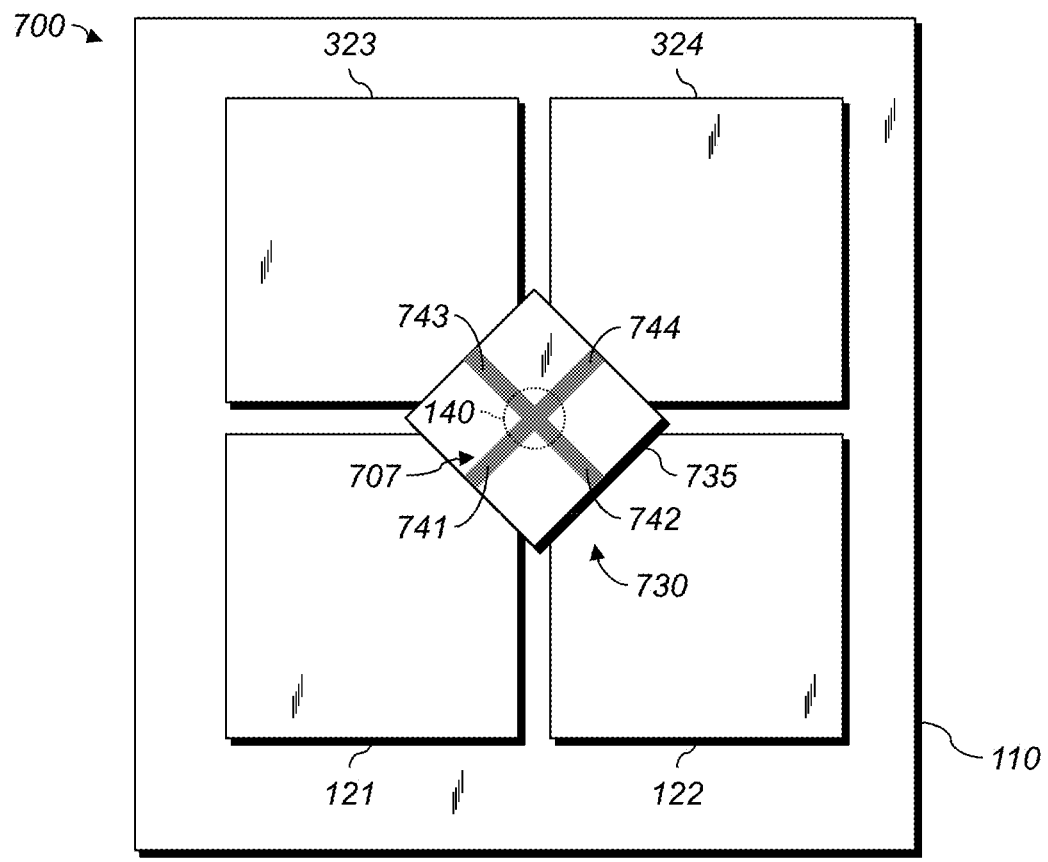
FIG. 7 is a plan view of an exemplary assay device in accordance with various embodiments.

Referring to FIG. 7, there is shown an exemplary assay device 700 having four test elements 121, 122, 323, and 324. A diverter 730 has a substrate 735 disposed at least partially in the common sample addition area 140, FIG. 1. The substrate 735 is configured to conduct the respective portions (not shown) of the fluidic sample 101, FIG. 1, to the at least two test elements 121, 122, 323, 324. In the example shown, the diverter 730 includes a plurality of microposts 707 (also referred to as "micropillars" or "projections") extending outwardly from the substrate 735 of the diverter 730. The microposts 707 have dimensions and spacing therebetween to induce lateral capillary flow of the respective portions to the at least two test elements 121, 122, 323, 324. The microposts 707 are arranged to define respective fluid flow paths 741, 742, 743, 744 leading to respective ones of the at least two test elements 121, 122, 323, 324. Further details of the construction and use of the microposts 707 and the fluid flow paths 741, 742, 743, 744 are discussed below with reference to FIG. 8.

As described above with reference to FIG. 2, parameters of the diverter 130 can be designed to provide respective, different amounts of fluid to different ones of the test elements 121, 122, 323, 324, or to control the points on the test elements 121, 122, 323, 324 first contacted by the respective portion of the metered sample 101. For micropost-based diverters such as the illustrated diverter 730, such parameters can include the spacing and arrangement of the microposts 707 and the widths, lengths, and curvatures of the fluid flow paths 741, 742, 743, 744.

Figure 8:
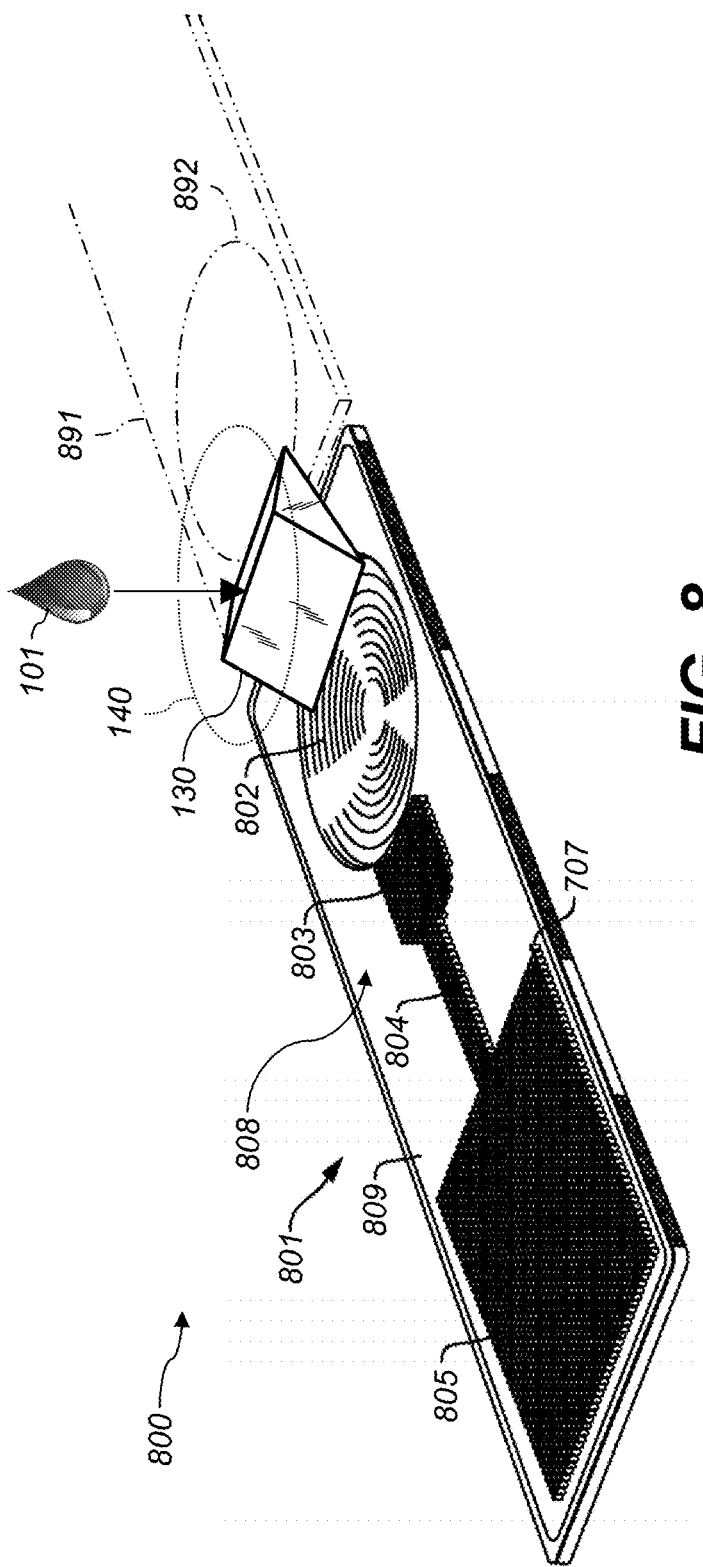
FIG. 8 is a perspective view of an exemplary assay device in accordance with various embodiments.

Referring to FIG. 8, there is shown an exemplary assay device 800 including a lateral-flow test element 801. Lateral-flow test elements 801 are another common type of disposable test element, just as dry slides are, and are also referred to as "lateral test strips." The term "lateral-flow assay device", as discussed herein, refers to any device that receives fluid, such as sample, and includes a laterally disposed fluid transport or fluid flow path 808 along which various stations or sites (zones) are provided for supporting various reagents, filters and the like through which sample, e.g., the fluidic sample 101 or a portion thereof, traverses under the influence of capillary or other applied forces and in which lateral-flow assays are conducted for the detection of at least one analyte of interest.

The exemplary test element 801 has at least one sample receiving zone 802, a reagent zone 803, at least one detection zone 804, and at least one wicking zone 805, each disposed on a nonporous common substrate 809. These zones are arranged along a defined flow path 808 by which sample, e.g., the fluidic sample 101 or a portion thereof, flows from the sample receiving zone 802 to the wicking zone 805 under the influence of capillary pressure provided between microposts 707 (also referred to as "micropillars" or "projections"). A plurality of the microposts 707 extend upwardly or otherwise outwardly from the substrate 809 and are disposed in the fluid flow path 808. The microposts 707 are defined dimensionally and in terms of their spacing to induce lateral capillary flow of a received fluidic sample 101 once the fluidic sample 101 or a portion thereof is introduced to the fluid flow path 808. Examples of such devices are disclosed in U.S. Pat. No. 8,025,854B2, WO 2003/103835, WO 2005/089082, WO2005/118139 and WO 2006/137785, all of which are incorporated by reference herein in their entireties.

In other examples, some lateral-flow test elements 801 can employ a porous material, e.g., nitrocellulose, in the fluid flow path 808 to support capillary flow of fluid. Examples include those devices shown in U.S. Pat. Nos. 5,559,041, 5,714,389, 5,120,643, and 6,228,660, all of which are incorporated herein by reference in their entireties.

Capture elements, such as antibodies, can be supported in the detection zone 804, these capture elements being capable of binding to an analyte of interest, the capture elements being deposited on the device, e.g., by coating. In addition, a labeled conjugate material, also capable of participating in reactions that will enable determination of the concentration of the analyte, is separately deposited on the lateral-flow test element 801 in the reagent zone 803, wherein the conjugate material carries a label for detection in the detection zone 804 of the lateral-flow test element 801.

The conjugate material is gradually dissolved as the fluidic sample 101, or a portion thereof, flows through the reagent zone, forming a conjugate plume of dissolved labeled conjugate material and fluidic sample 101 that flows downstream along the defined fluid flow path 808 of the lateral-flow test element 801 to the detection zone 804. As the conjugate plume flows into the detection zone 804, the conjugated material will be captured by the capture elements such as via a complex of conjugated material and analyte (e.g., as in a "sandwich" assay) or directly (e.g., as in a "competitive" assay). Unbound dissolved conjugate material will be swept past the detection zone 804 and into the wicking zone 805.

An instrument such as that disclosed in US 2006/0289787A1, US 2007/0231883A1, U.S. Pat. No. 7,416,700 and U.S. Pat. No. 6,139,800, all incorporated by reference in their entireties herein, is configured to detect the bound conjugated material in the detection zone 804. Common labels include fluorescent dyes that can be detected by instruments which excite the fluorescent dyes and incorporate a detector capable of detecting the resulting fluorescence.

In the foregoing devices and in the conduction of assays, the resulting level of signal in the detection zone 804 is read using a suitable detection instrument after the conjugate material has been dissolved and sample, e.g., the fluidic sample 101 or a portion thereof, and unbound conjugate material and, optionally, wash fluid added to a reagent zone 803 of the lateral-flow test element 801 has reached and subsequently filled the wicking zone 805 of the lateral-flow test element 801.

According to at least one version, therefore, the two or more test elements 121, 122, FIG. 1, include at least one lateral-flow test element 801. An assay device 100 can include only dry-slide test elements, or can include only lateral test elements, or can include any number of either dry-slide or lateral test elements. In this version, the support 110, FIG. 1, can include, e.g., a bracket retaining the lateral-flow test element 801 in position with respect to a dry slide test element or another lateral-flow test element.

Specifically and in an exemplary aspect, the lateral-flow test element 801 includes the substrate 809 having the sample receiving zone 802 configured to direct sample, e.g., the fluidic sample 101 or a portion thereof, along the fluid flow path 808. The diverter 130 is arranged to conduct a respective portion of the fluidic sample 101 from the common sample addition area 140, FIG. 1, to the sample receiving zone 802. In another exemplary aspect, two or more of the test elements 121, 122 are lateral-flow test elements 801 having the respective sample receiving zones 802. The diverter 130 is arranged to conduct respective portions (not shown) of the fluidic sample 101 from the common sample addition area 140 to the sample receiving zones 802 of each of the lateral-flow test elements 801.

In various configurations, at least one of the at least two test elements 121, 122, FIG. 1, includes the substrate 809 having the plurality of microposts 707 (projections) outwardly extending from the upper surface (shown) of the substrate 809 along the defined fluid flow path 808 including the sample receiving zone 802 in relation to the common sample addition area 140. The microposts 707 (projections) have dimensions and a relative spacing between the projections that induce lateral capillary flow of a received fluidic sample 101. For example, the at least one of the at least two test elements 121, 122 can be the lateral-flow test element 801. In various configurations, a plurality of the at least two test elements 121, 122 can be lateral-flow analytical test elements 801.

As shown, in an embodiment the assay device 800 includes the diverter 130. In at least one example and as shown in phantom, the assay device 800 also includes a second lateral-flow test element 891 arranged so that its sample receiving zone 892 is placed in operative relation to the common sample addition area 140 to receive a respective portion of the fluidic sample 101. In the specific configuration illustrated, the diverter 130 includes a wedge that divides the fluidic sample 101 into two roughly equal portions. Each portion flows down a respective side of the wedge in the diverter 130 to a respective one of the sample receiving zones 802, 892.

Various configurations of lateral-flow test elements, e.g., the lateral-flow test elements 801, 891, include plastic or other sample-impermeable covers (not shown) mounted over the respective substrates 809. In these configurations, the diverter 130 can be formed as part of, or mounted to, one or more of those covers.

Figure 9A:
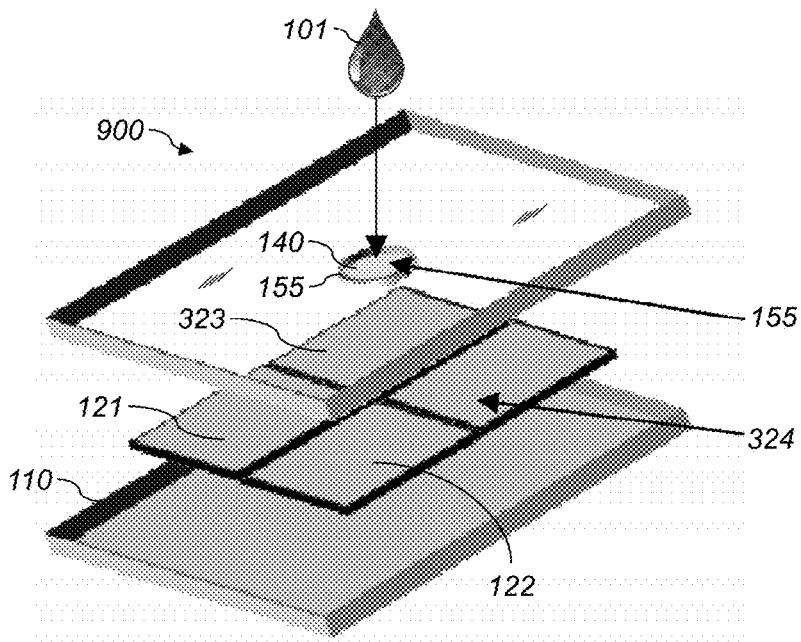
FIG. 9A is a perspective view, and FIG. 9B a top view, of an exemplary assay device in accordance with various embodiments.
Figure 9B:
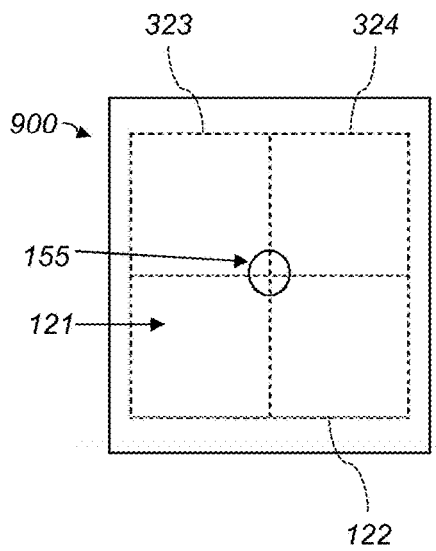

Referring to FIGS. 9A and 9B, there are shown a perspective and a top view, respectively, of an exemplary assay device 900 having a support 110 and at least two test elements 121, 122, 323, 324 disposed over the support 110 at least partly in proximity to each other to define a common sample addition area 140. At least one of the at least two test elements 121, 122, 323, 324 is a dry slide analytical test element. In the illustrated configuration, the at least two test elements 121, 122, 323, 324 are in abutting relation with each other.

In various embodiments, the assay device 900 is configured so that the at least two test elements 121, 122, 323, 324 all receive respective portions of the fluidic sample 101 with a single metered fluidic sample 101. This can permit quadrupling the throughput of an analyzer by providing four test results with a single analyzer actuation. In various versions, the fluid sample 101 is metered through the aperture 155 or otherwise metered onto the common sample addition area 140. The at least two test elements 121, 122, 323, 324 abut or otherwise fluidically interface with each other in the common sample addition area 140 to receive the metered fluidic sample 101. The gaps between the test elements 121, 122, 323, 324, or the metered volume of the fluidic sample 101, can be adjusted to control flow rate and leakage.

In an example, four VITROS ECO2 chemistry chips (the test elements 121, 122, 323, 324) were mounted adjacent to one another according to one example shown in FIG. 9A. A single 10 µL drop of VITROS Drop Volume Fluid (the fluidic sample 101) was metered directly on the intersection of the test elements 121, 122, 323, 324 using a VITROS 5,1 FS analyzer. The metered fluid flowed on all four test elements 121, 122, 323, 324. That is, all four test elements 121, 122, 323, 324 received respective portions of the fluidic sample 101 from the single metering event at the common sample addition area 140, which included the intersection of the four test elements 121, 122, 323, 324. This experiment demonstrates that multiple ones of the test elements 121, 122, 323, 324 (or any number of test elements) can receive portions of the single fluidic sample 101 dispensed in a single sample metering event. Other exemplary chemistry chips that can be used as ones of the test elements 121, 122, 323, 324 with various embodiments include the VITROS Ca, Cl—, Crea S, Crea U, Gluc CSF, Gluc S, and Gluc U chips. In at least one aspect, each of the test elements 121, 122, 323, 324 (or each of the test elements used in a particular assay device, regardless of the number of those test elements) includes a different chemistry chip or reagent, or otherwise performs a different assay from the other test elements in that assay device.

Figure 10:
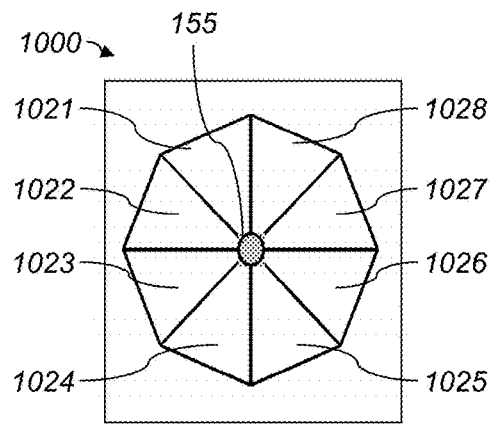
FIG. 10 is a top view of an exemplary assay device in accordance with various embodiments.

Referring to FIG. 10, there is shown an exemplary assay device 1000 using a triangular geometry of the test elements 1021-1028. In such configurations, more test elements 1021-

1028 can be spotted with a single metering event than can in configurations using rectangular chip geometry, e.g., FIGS. 8A-8B. The assay device 1000 includes eight test elements 1021, 1022, 1023, 1024, 1025, 1026, 1027, 1028 arranged roughly circularly around the common sample addition area 140 (FIG. 8A) underneath the aperture 155.

The assay devices 800, 1000 can be used with analyzers designed for direct spotting on multiple test elements 801, 891, 1021-1028 at an intersection or interface between those test elements 801, 891, 1021-1028. For example, the volume of the fluidic sample 101 can be selected so that the metered fluidic sample 101 spreads to a drop having a diameter large enough to cover a portion of each of the test elements 1021-1028. Each of the test elements 121, 122, 323, 324, 1021-1028 can include a spreading layer to convey the respective portion of the metered sample 101 from the common sample addition area 140, FIG. 1, across that one of the test elements 121, 122, 323, 324, 1021-1028.

As noted above with reference to FIG. 1A, each of the test elements 121, 122, 323, 324, 1021-1028 can include the chemically-active portion of a conventional dry slide assay device. Each of the test elements 121, 122, 323, 324, 1021-1028 can also include other components of such an assay device, e.g., a support thereof.

Figure 11:
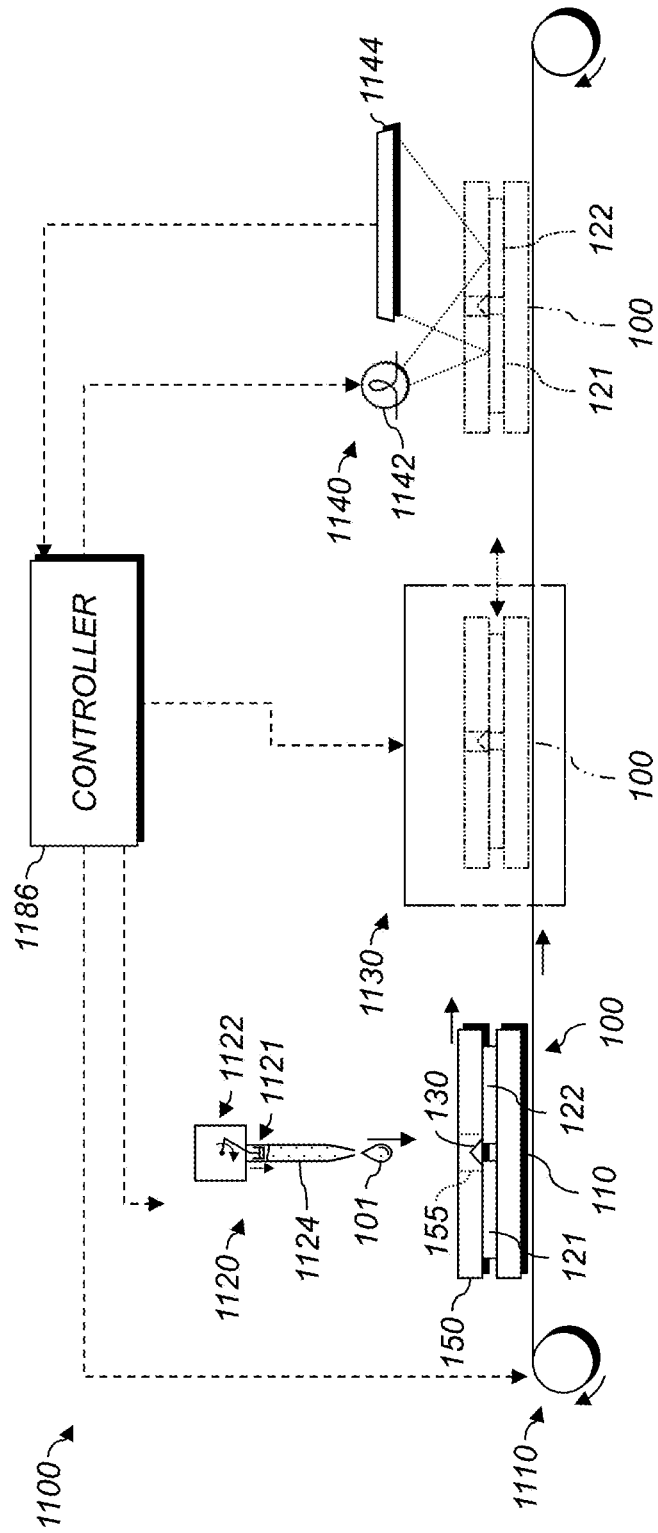
FIG. 11 is a schematic view of an apparatus for analyzing a fluidic sample according to at least one exemplary embodiment, and related components.

Referring to FIG. 11, there is shown an apparatus 1100 for analyzing a fluidic sample 101 according to at least one exemplary embodiment. The apparatus 1100 includes a transport system 1110 for conveying the assay device 100 between components described below. For simplicity, the transport system 1110 is represented as a continuous conveyor belt. However, this is not limiting. The transport system 1110 can include conveyor(s), gripper(s), robotic arm(s), or other device(s) for moving the assay device 100 with respect to below-described components, or can include stage(s), conveyor(s), or other device(s) for moving below-described components with respect to the assay device 100, in any combination. Various examples of the transport system 1110 are described in commonly-assigned U.S. Pat. No. 8,080,204 to Ryan et al. and U.S. Pat. No. 8,043,562 to Tomasso et al., each of which is incorporated herein by reference, and in the above-noted U.S. Pat. No. 7,632,468 to Barski, et al, already incorporated by reference. Positions of the assay device 100 at various stages of processing are shown in phantom.

In this example, the assay device 100 includes the support 110 and the least two test elements 121, 122, as described above with reference to FIG. 1B. Any of the above-described embodiments of assay devices can be used in addition to or in place of the assay device 100, e.g., the assay devices 200, 300, 500, 600, 700, 800, 1000, 1200. At least one of the at least two test elements 121, 122 is a dry slide analytical test element.

A metering mechanism 1120 is configured to selectively apply the fluidic sample 101 to the at least one assay device 100. The illustrated metering mechanism 1120 includes a metering tip 1124 holding, e.g., 250 µL of the fluidic sample 101. The metering tip 1124 can be, e.g., a disposable tip or a washable or otherwise reusable tip. In various aspects, there is a one-to-one correspondence between a particular fluidic sample 101 and a particular metering tip 1124. In an example, each metering event meters between ~5 µL and ~10 µL of the fluidic sample 101.

In the illustrated example, and for explanation only, the metering mechanism 1120 includes a piston 1121 and a driving system 1122 operating the piston 1121 to dispense a selected volume of the fluidic sample 101 from the metering tip 1124. Other structures for metering can also be used, e.g., air or fluid pressure sources or piezoelectric or thermal actuators. An exemplary metering tip 1124 is described in U.S. Publication No. 2004/0072367 by Ding, et al., the disclosure of which is incorporated herein by reference. Metering onto a test element 121, 122 is referred to herein as "spotting."

The exemplary apparatus 1100 includes at least one incubator 1130. Various types of sample testing, including potentiometric, rate chemistry, and endpoint tests, may be required for any given patient sample, necessitating both different incubation intervals and different test apparatus within the incubator 1130. Accordingly, more than one incubator, or a tandem or other multi-test-capable incubator can be used. For clarity, only one incubator 1130 is shown. Various examples of incubators 1130 and related components are described in U.S. Pat. No. 4,287,155 and U.S. Pat. No. 7,312,084 to Jakubowicz, et al., entitled "Tandem Incubator for Clinical Analyzer," each of which is hereby incorporated by reference in its entirety.

The incubator 1130 retains the assay device(s) 100, e.g., at room temperature or under selected environmental conditions, until an accurate measurement can be taken. Some assay devices 100 require endpoint testing, which requires only a single read be performed following a predetermined incubation interval (e.g., approximately 5 minutes). Other assay devices 100, such as those requiring rate chemistries, require a number of reads to be taken throughout the course of incubation. The incubator 1130 or the transport system 1110 can therefore include structures for transporting assay device(s) 100 between the incubator 1130 and a measurement device 1140, discussed below.

In an exemplary embodiment, the incubator 1130 includes a rotor assembly (not shown) that includes a single rotatably driven ring (not shown) having a plurality of circumferentially disposed load stations. Each of the load stations is sized to accommodate an assay device 100 onto which a quantity of the fluidic sample 101 has been metered. According to at least one version of a dry-type incubator, the assay devices 100 are supplied one at a time to the metering mechanism 1120, which can be arranged adjacent to the incubator 1130. After the fluidic sample 101 has been metered onto a given assay device 100, that assay device 100 is shuttled or otherwise introduced into an empty load station (not shown) of the incubator 1130, such as through use of a reciprocating pusher blade (not shown), as the rotor assembly advances the next empty load station into position for receiving the next-metered assay device 100.

The exemplary apparatus 1100 shown further includes at least one measurement device 1140. The measurement device 1140 can include a potentiometric sensor, e.g., a voltmeter, ammeter, or charge meter, or a colorimetric or other photometric sensor. Exemplary photometric sensors include photodiodes and line-scan or area-scan reflectometers or imagers, e.g., charge-coupled device (CCD) or complementary metal-oxide-semiconductor (CMOS) imagers. Colorimetric sensors can operate in reflective or transmissive modes. Reflective colorimetric sensors can be arranged to measure the front or back of the assay device 100, i.e., to measure the side of the test elements 121, 122 facing the cover 150 or the side facing the support 110.

In an example, the measurement device 1140 includes a light source 1142 (represented graphically as a lamp). The light source 1142 can include a lamp, light-emitting diode (LED), laser, or other source of optical radiation. The exemplary measurement device 1140 also includes a line-scan imager 1144 that captures an image line extending across the test elements 121, 122, e.g., along the line IB-IB shown in FIG. 1A. In the example shown, light from the light source 1142 strikes the test elements 121, 122 and reflects back to the line-scan imager 1144. Examples of data from such a measurement process are shown in FIGS. 14B, 15B, discussed below.

The exemplary apparatus 1100 further includes a controller 1186 configured to operate each of the metering mechanism 1120, the incubator 1130, and at least one measurement device 1140 in accordance with a predetermined timing protocol in order to determine at least one characteristic of the applied fluidic sample 101. For clarity only, communications connections between the controller 1186 and other components are shown dashed. Further and according to this exemplary embodiment, the controller 1186 is configured to operate the transport system 1110. For example, the controller 1186 can sequence the motion of the assay device 100 through the metering mechanism 1120, the incubator 1130, and at least one measurement device 1140 to perform a potentiometric or colorimetric measurement of the fluidic sample 101. The exemplary controller 1186 is further configured to receive data from the line-scan imager 1144 and provide a graphical representation of the measured data via an electronic display. The controller 1186 can include various components discussed below with reference to FIG. 16, e.g., a processor 1686 or a peripheral system 1620.

In various aspects, the assay device 100 is configured substantially as shown in FIG. 2B. In these exemplary aspects, the assay device 100 includes the defined common sample addition area 140, FIG. 2B, arranged in relation to the at least two test elements 121, 122. The exemplary assay device 100 also includes the single porous member 230, FIG. 2B, arranged at least partly over each of the test elements 121, 122 and at least partly in the common sample addition area 140. The porous medium 230 is configured to convey the fluidic sample 101 from the common sample addition area 140 to each of the at least two test elements 121, 122, as discussed above.

In various embodiments, the assay device 100 is configured substantially as shown in FIG. 1A. In these exemplary embodiments, the assay device 100 further includes the defined common sample addition area 140, FIG. 1A, arranged in relation to the at least two test elements 121, 122. The assay device 100 further includes the diverter 130 arranged at least partly in the common sample addition area 140 and including a plurality of surfaces (the faces 131, 132, FIG. 1A) defining respective fluid flow paths (not shown) extending from the common sample addition area 140 to each of the at least two test elements 121, 122, e.g., extending over the inclined faces of the diverter 130, FIG. 1A.

Figure 12:
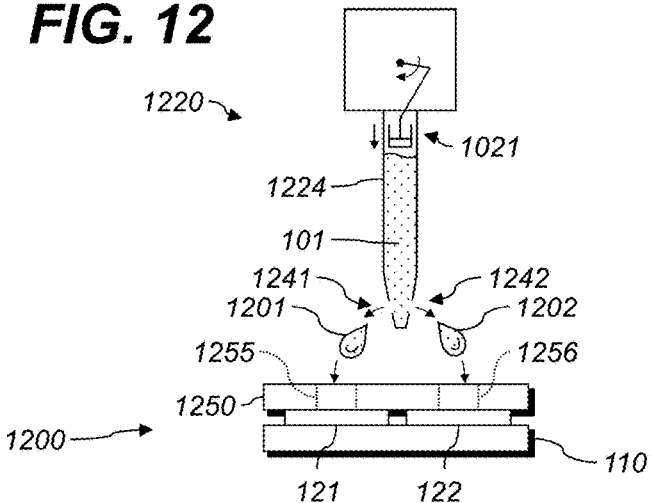
FIG. 12 is a schematic view of an exemplary metering mechanism and an exemplary assay device according to an embodiment.

FIG. 12 shows an exemplary metering mechanism 1220 and an exemplary assay device 1200. In this example, the assay device 100 includes the support 110 and the test elements 121, 122 as discussed above with reference to, e.g., FIG. 1A. Arranged over the test elements 121, 122 in this exemplary configuration is a cover 1250 having two apertures 1255, 1256, one over each of the test elements 121, 122. The exemplary assay device 1200 does not have a diverter 130, FIG. 1A.

The exemplary metering mechanism 1220 comprises a metering tip 1224 configured to dispense fluid of the fluidic sample 101. In this example, the metering tip 1224 is closed at the end, as shown, and has a plurality of apertures 1241, 1242 configured to dispense the fluidic sample 101 in a plurality of different directions. Two portions 1201, 1202 of the fluidic sample 101 are shown traveling away from the metering tip 1224 under pressure from the piston 1121, or in response to other dispensing actuations described above, and after passage through the apertures 1241, 1242, respectively. The metering mechanism 1220 can be used in place of or in addition to the metering mechanism 1120, FIG. 11. In such configurations, the apparatus 1100, FIG. 11, further comprises a subsystem, e.g., the transport system 1110, for operatively arranging the assay device 1200 with respect to the metering tip 1224 so that each of the at least two test elements 121, 122 corresponds to a respective one of the directions of fluid dispensing. In the example of FIG. 12, the portion 1201 of the fluidic sample 101 is dispensed from the metering tip 1224 and reaches the test element 121 via the aperture 1255. The portion 1202 reaches the test element 122 via the aperture 1256.

In other configurations, the metering tip 1224 can include a diverter (not shown) internal or external to the metering tip 1224. For example, the metering tip 1224 can dispense fluid through a single aperture (as does the metering tip 1124, FIG. 11; not shown in FIG. 12) onto a pyramidal or other diverter (not shown) suspended below that aperture.

In various aspects using the metering mechanism 1220, a method of analyzing a fluidic sample 101 includes operatively arranging the assay device 1200 having the two or more test elements 121, 122 with respect to the metering mechanism 1220 having the metering tip 1224 configured to dispense fluid of the fluidic sample 101 in a plurality of different directions (in this illustration, one direction is to the left and the other direction is to the right), The fluidic sample 101 is then dispensed directly to the test elements 121, 122 from the metering tip 1224, e.g., as the portions 1201, 1202. The test elements 121, 122 are then measured, e.g., using the measurement device 1140, FIG. 11, to determine the presence of a detectable signal corresponding to a characteristic of the metered fluidic sample 101 relative to each of the test elements 121, 122. Further details of this and other methods of analyzing the fluidic sample 101 are discussed below with reference to FIG. 13.

Figure 13:
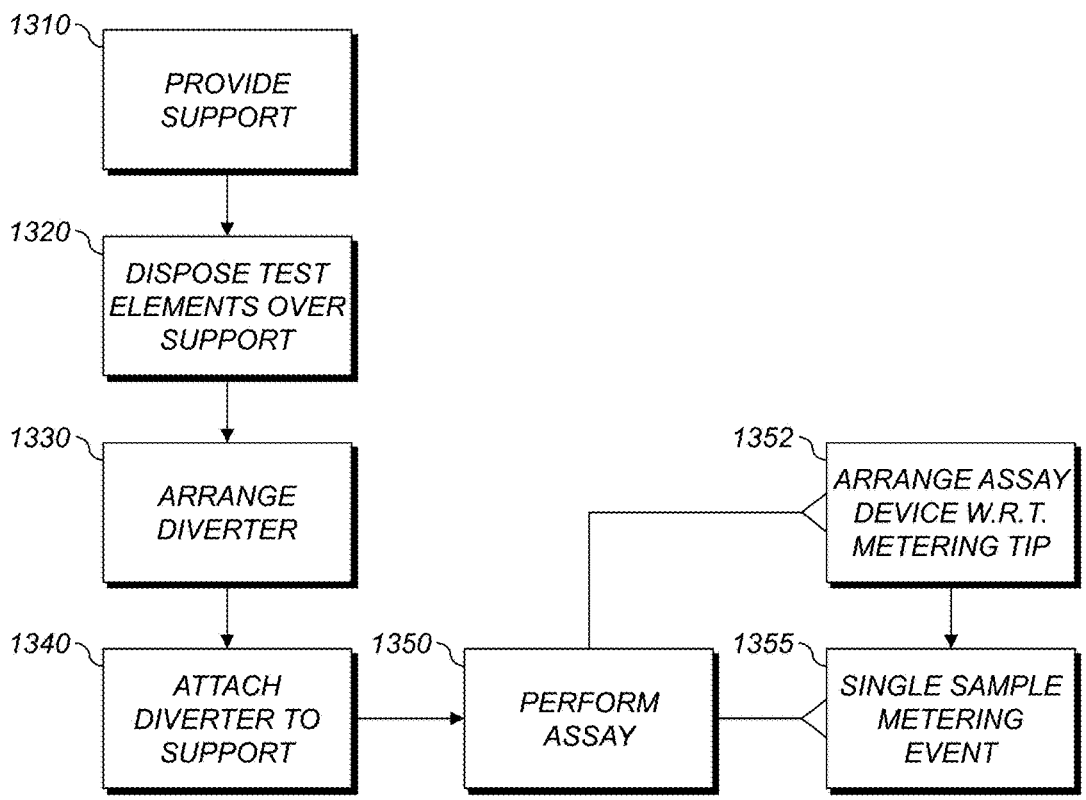
FIG. 13 shows a flowchart illustrating exemplary methods for enabling an assay device to perform multiple tests based upon a single sample metering event in accordance with various embodiments.

FIG. 13 shows a flowchart illustrating exemplary methods for enabling an assay device, e.g., the assay device 100, FIG. 1, to perform multiple tests based upon a single sample metering event. The steps can be performed in any order except when otherwise specified, or when data or structures from an earlier step are used or referred to in a later step. In at least one example, processing begins with step 1310. For clarity of explanation, reference is herein made to various components shown in FIGS. 1A-12 that can carry out or participate in the steps of the exemplary method. It should be noted, however, that other components can be used; that is, exemplary method(s) shown in FIG. 13 are not limited to being carried out by the identified components.

In step 1310, a support of the assay device 100 is provided. This can be, e.g., the support 110, FIG. 10. The support 110 can be provided, e.g., by an assembly robot under the control of a processor such as a processor 1686, FIG. 16.

In step 1320, at least two test elements, e.g., the test elements 121, 122, FIG. 10, are disposed over the support 110. This can be done, e.g., by an assembly robot under the control of a processor 1686. In this way, a common sample addition area is defined, e.g., the common sample addition area 140, FIG. 9A. At least one of the at least two test elements 121, 122 is a dry slide analytical test element such as those described above. Moreover, the at least two test elements 121, 122 are configured to receive respective portions of a single fluidic sample 101, FIG. 11, metered from a fluid supply during the single sample metering event onto the common sample addition area 140. At least one of the two or more test elements 121, 122 can be a lateral-flow assay device, in at least one exemplary configuration.

In various examples, the fluid supply can be or include, e.g., the metering mechanism 1120, FIG. 11. The fluid supply can include a metering tip 1124, FIG. 11, or a metering tip 1224, FIG. 12. The single sample metering event can be dispensing of the fluidic sample 101, FIG. 10, through e.g., a single sample drop hole or an aperture 155, FIG. 10, of the assay device 100. Step 1320 can be followed by step 1330.

Step 1330, in various aspects, includes arranging a diverter in relation to the at least two test elements 121, 122 to define the common sample addition area 140 of the assay device 100. The diverter can be the diverter 130, FIG. 10. The diverter 130 is configured to conduct respective portions of the fluidic sample 101 from the common sample addition area 140 to each of the at least two test elements 121, 122. In an example, the diverter 130, e.g., as shown in FIG. 4, includes a polyhedral configuration including a plurality of the faces 421-425 disposed in relation to each of the at least two test elements 121, 122 and configured such that applied sample, e.g., each respective portion of the fluidic sample 101, flows along the respective face 421-425 to a corresponding one of the at least two test elements 121, 122. In another example, the diverter 130, e.g., as shown in FIG. 2A, includes a porous member 230 arranged at least partly over each of the at least two test elements 121, 122. Step 1330 can be followed by step 1340.

Step 1340, in various aspects, includes attaching the diverter 130 to the support 110. The diverter 130 can be, e.g., glued, welded, or otherwise bonded to the support 110. In other aspects, step 1340 includes attaching the diverter 130 to the cover 150, FIG. 10. Step 1340 can be followed by step 1350.

Step 1350, in various aspects, includes performing an assay using the enabled assay device 100 prepared in steps 1310, 1320, 1330, 1340, in various combinations. Step 1350 can include metering, incubating, and measuring, as described above with reference to FIG. 11. In an exemplary embodiment, at least one of the two or more test elements 121, 122 is configured to produce a detectable signal in response to a characteristic of the respective portion of the dispensed fluidic sample 101. The detectable signal can be, e.g., detectable visually or potentiometrically. Visual detection can be performed, e.g., by a human or a computerized machine-vision system. In at least one example, step 1350 includes step 1352, step 1355, or both. This is graphically represented by the open triangular terminators at steps 1352, 1355.

Still referring to FIG. 13, and referring also to FIG. 12, in step 1352, the assay device 1200 is operatively arranged with respect to a metering tip 1224 configured to dispense fluid in a plurality of different directions. Each of the at least two test elements 121, 122 of the arranged assay device 1200 corresponds to a respective one of the directions. For example, step 1352 can include positioning the assay device 1200 under the metering tip 1224 as shown in FIG. 12.

Still referring to FIG. 13 and referring also to FIGS. 11 and 12, in step 1355, a single sample metering event is performed. That is, a selected amount of the single fluidic sample 101 is dispensed from the metering mechanism 1120 or 1220. The fluidic sample 101 is divided by a diverter 130, e.g., in the assay device 100, or by a metering tip 1224. As a result, portions of the dispensed fluidic sample 101 reach the respective test elements 121, 122, as described above. An exemplary diverter 130 is a porous member 230 onto which the single fluidic sample 101 is dispensed. In examples using step 1352, the respective portions 1201, 1202 of the single fluidic sample 101 travel in the respective directions and reach the respective ones of the at least two test elements 121, 122.

Figure 14A:
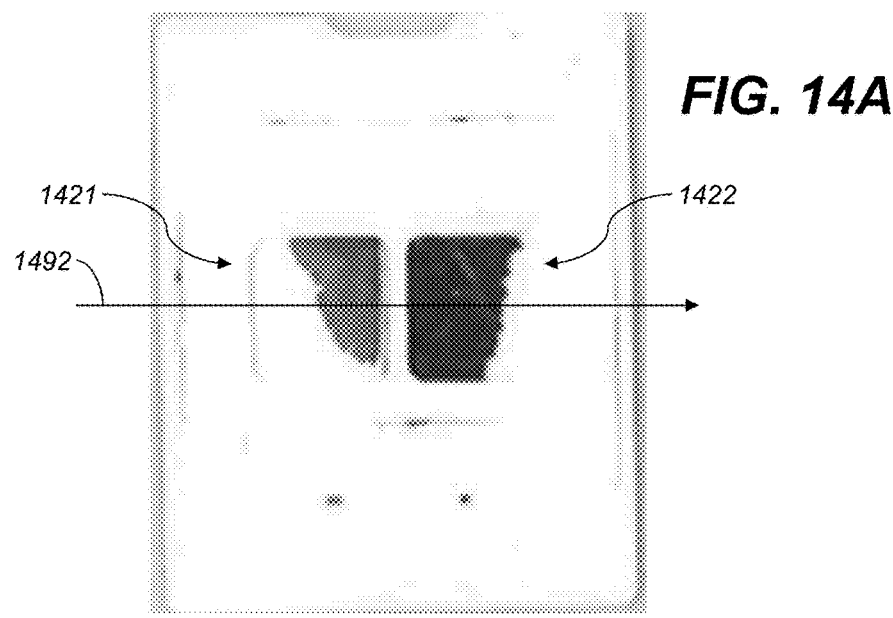
FIGS. 14A-14B show exemplary measured data of an assay device constructed according to an embodiment.
Figure 14B:
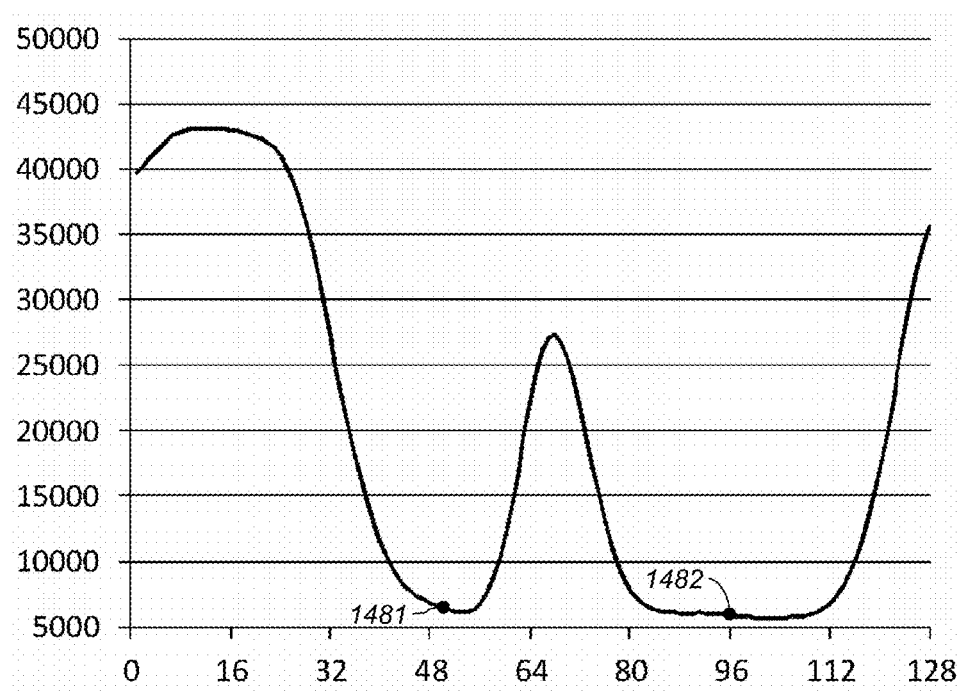

Referring to FIGS. 14A-14B, there is shown exemplary measured data of an assay device according to various embodiments. An assay device was prepared as described above with reference to FIGS. 2A-2C. Two of the test elements 1421, 1422, namely a VITROS cholesterol (CHOL) chip (1421) and a VITROS triglyceride (TRIG) chip (1422), were mounted in the support 110, which included a molded frame with the center one third of the separation post on the spreadlayer side (i.e., the side facing up in FIG. 2A) removed. In the center post gap, a porous member 230, namely a small piece of Whatman filter paper, was placed perpendicular to the post and across the two test elements 1421, 1422. A single 10 μL drop of VITROS Performance Verifier II was metered directly on the filter paper (the porous member 230) and the assay device was incubated and read at 540 nm following the standard VITROS time template (~5 minutes) for these chemistries on a VITROS 5,1 FS analyzer. The assay device was collected from the analyzer and the bottom of the assay device (the read side) was scanned.

FIG. 14A is a labeled graphical representation of the scanned image showing that both test elements 1421, 1422 were spotted from (i.e., received fluidic sample 101 from) the metered filter paper. This can be seen by the formation of the illustrated dark dye in the reaction cascade. The raw analogue to digital (A/D) signal response was read across the assay device (128 reads, 0.7 msec spacing between reads), approximately along the line 1492.

FIG. 14B is a plot of A/D counts as a function of read number, i.e., as a function of position along the line 1492, FIG. 14A. FIG. 14B shows that a signal response correlating to the two spotted test elements 1421, 1422 was observed. The spotted CHOL test element 1421 on the left hand side of the assay device in FIG. 14A gives an A/D reflectance response centered at ~read 50 (indicated as point 1481) while the spotted TRIG test element 1422 on the right hand side of the assay device in FIG. 14A gives an A/D reflectance response centered at ~read 96 (point 1482). The width of the signal in FIG. 14B correlates well to the width of the spotted assay device shown in FIG. 14A. This example shows that two different chemistry chips (the test elements 1421, 1422) were effectively spotted with portions of the fluid sample 101 dispensed by a single sample metering event onto the filter paper (the porous member 230) spanning the two chemistry chips. The size and position of the porous member 230, and the volume of the fluidic sample 101, can be co-optimized to improve performance.

Figure 15A:
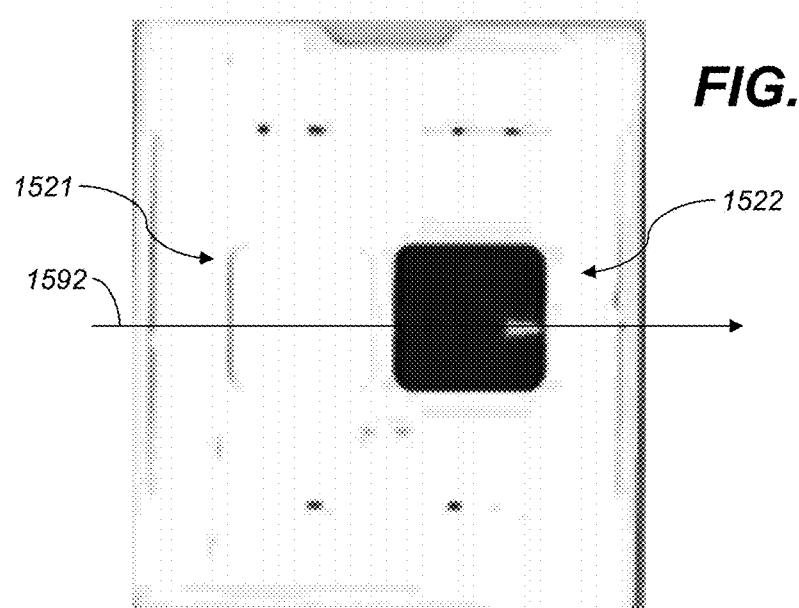
FIGS. 15A-15B show exemplary measured data of an assay device constructed according to an embodiment.
Figure 15B:
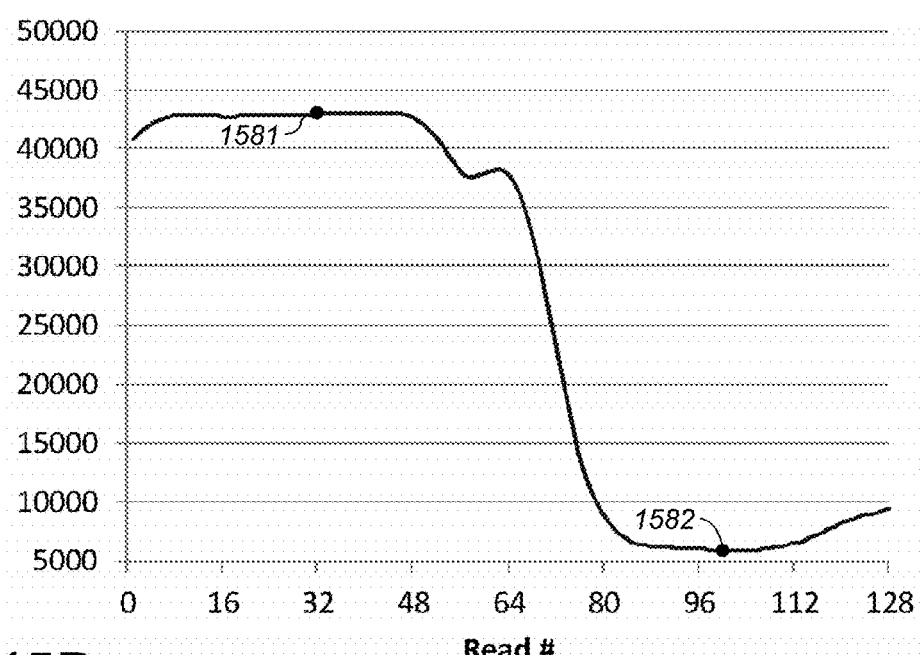

Referring to FIGS. 15A-15B, there is shown exemplary measured data of an assay device according to various embodiments. An assay device was prepared as described above with reference to FIG. 6. Two of the test elements 1521, 1522, namely a VITROS CHOL chip (1521) and VITROS TRIG chip (1522) were mounted in the support 110, namely the base of a molded frame. The frame included a cover with two drop apertures 621, 622, FIG. 6. The center one-third of the separation post between the drop apertures 621, 622 on the spreadlayer side was scraped off at an angle towards the TRIG test element 1522. The scraped portion of the separation post thus corresponded to the splitter 632, FIG. 6, only with a slope directing fluid into the drop aperture 622 but not into the drop aperture 621. Accordingly, the cover of the assay device corresponded to the diverter 630, FIG. 6. A single 10 μL drop of VITROS Performance Verifier II was metered directly on the shaved plastic bridge (the splitter 632) and the assay device was incubated and read at 540 nm following the standard VITROS time template (~5 minutes) for these chemistries on a VITROS 5,1 FS analyzer. The assay device was collected from the analyzer and the bottom of the assay device (the read side) was scanned.

FIG. 15A is a labeled graphical representation of the scanned image showing that only the TRIG chemistry chip (right hand side, the test element 1522) was spotted. That is, the metered fluidic sample 101 directionally flowed as designed. This is indicated by the formation of the dye in the reaction cascade of the test element 1522. The spotted test element 1522 was not completely uniform due to a small defect on the TRIG spreadlayer (white spot on the test element 1522 image). The raw analogue to digital (A/D) signal response was read across the assay device (128 reads, 0.7 msec spacing between reads), approximately along the line 1592.

FIG. 15B is a plot of A/D counts as a function of read number, i.e., as a function of position along the line 1592, FIG. 15A. FIG. 15B shows that a signal response correlating to only the TRIG test element 1522, FIG. 15A, was observed and no signal was observed on the CHOL test element 1521, FIG. 15A. The center of the CHOL test element 1521 is located at ~read 32 (point 1581) while the center of the TRIG test element 1522 is located at ~read 100 (point 1582) where there is a large decrease in the A/D counts due to the dye absorbance. This example shows that flow of the fluidic sample 101 can be directed with a bridge structure, e.g., the diverter 630 having the splitter 632, from a single sample metering event on the splitter 632. More complex bridge structure such as those described in FIGS. 1A, 1B, 3-5, 7, and 8 can be produced to meter multiple chips from a single metering event. A unique feature of various aspects is that the assay commences or is triggered without any direct metering on the test elements 1521, 1522.

In view of the foregoing, various aspects provide assay devices and analyzers that permit concurrently conducting multiple tests or assays on a single fluidic sample 101 using a single sample metering event. A technical effect of various aspects is to control the operation of components of an analyzer to perform metering, incubation, and measurement of physical assay devices 100 and fluidic samples 101, e.g., human blood samples. A further technical effect is to present a visual representation of measured assay data, e.g., representations such as those shown in FIGS. 14A-15B, on an electronic display 1635, FIG. 16.

Moreover, various embodiments described herein advantageously overcome limitations on the throughput of the analyzer apparatus 1100 due to metering cycle limitations. In an example, some present-day VITROS analyzers can meter the fluidic sample 101 no more frequently than every r seconds, where r can be, e.g., 4.75 sec (for a two-incubator analyzer) or 9.5 sec (for a one-incubator analyzer). A metering event can take, e.g., 1 sec. Multiplexing metering of the fluidic sample 101 across two of the test elements 121, 122 as described herein can advantageously double test throughput of such a VITROS analyzer. Multiplexing the fluidic sample 101 across more than two of the test elements can further increase test throughput, e.g., proportionately to the number of the test elements included in each assay device. Moreover, various embodiments herein can be used with any automated, bench top, or hand held analyzer to increase throughput without substantially increasing metering actuations. This can ease the timing-cycle requirements of such analyzers, permitting improvements in other aspects of analyzer performance to be made without running afoul of timing constraints. Moreover, throughput can be further increased in at least one example by metering multiple spots per r seconds, and performing multiple tests per spot per assay device 100 as described herein.

Exemplary full-panel assay devices according to various aspects include Basic Metabolic Panel, Comprehensive Metabolic Panel, and Lipid Panel, as noted above. An exemplary Basic Metabolic Panel assay device includes seven test elements respectively configured to measure the following properties of a blood fluid sample 101: glucose, calcium, sodium, potassium, carbon dioxide, chloride, blood urea nitrogen, and creatinine. An exemplary Lipid Panel assay device includes four test elements respectively configured to measure the following properties of a blood fluid sample 101: total cholesterol, high-density lipoprotein cholesterol, low-density lipoprotein cholesterol, and triglycerides. An exemplary Comprehensive Metabolic Panel assay device includes 14 test elements respectively configured to measure the following properties of a blood fluid sample 101: glucose, blood urea nitrogen, serum creatinine, sodium, potassium, chloride, carbon dioxide, calcium, total protein, albumin, total globulin, total bilirubin, alkaline phosphatase, and aspartate aminotransferase. In one embodiment, the 14 tests in a Comprehensive Metabolic Panel are spread over two assay devices, each having seven test elements. In general, any panel or multi-assay protocol can be divided over more than one assay device, the number of such assay devices being fewer than the total number of assays in the protocol (e.g., fewer than 14 assay devices for a Comprehensive Metabolic Panel). This provides increased throughput of tests with less-complex assay devices.

Figure 16:
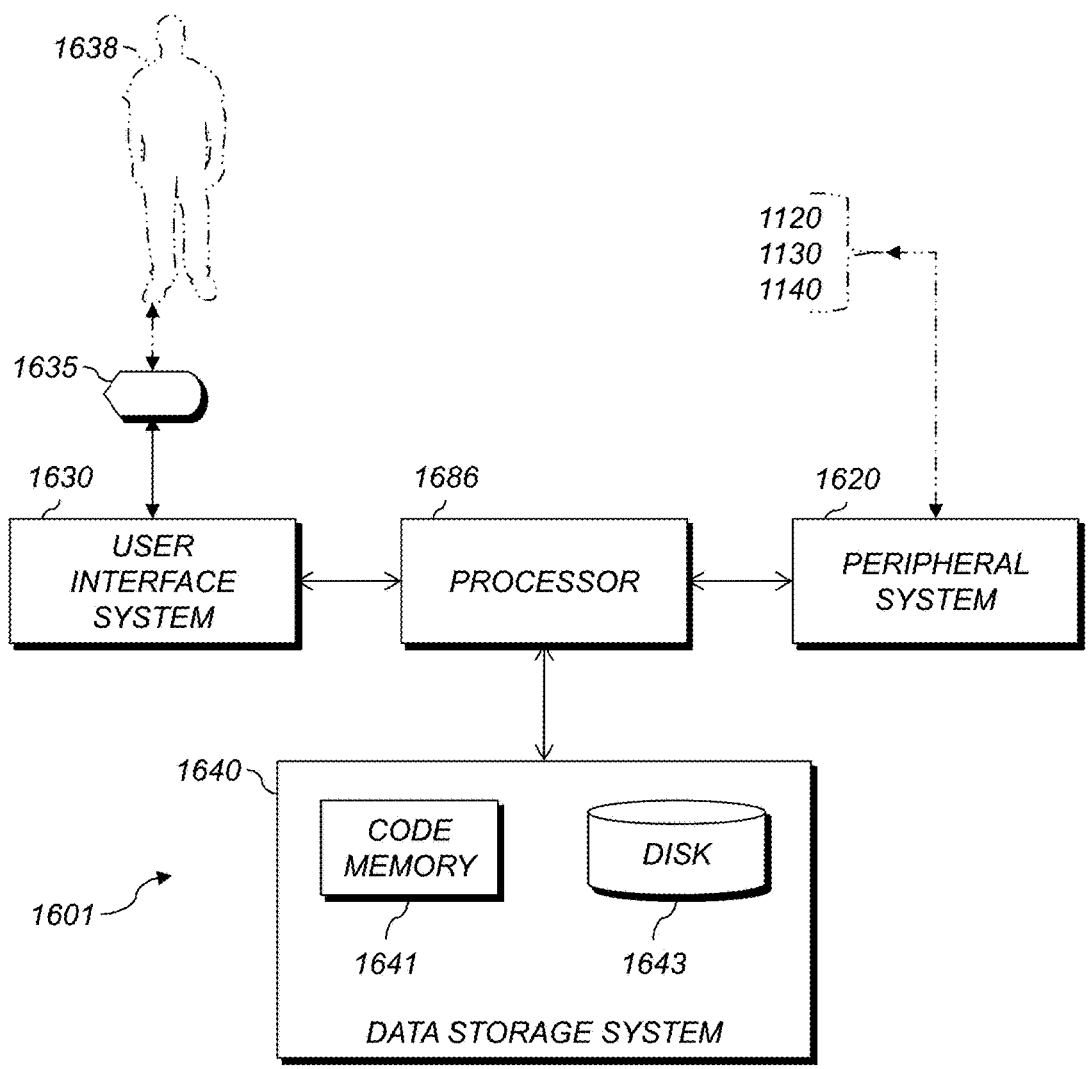
FIG. 16 is a high-level diagrammatic view showing components of a data-processing system in accordance with various embodiments.

FIG. 16 is a high-level diagram showing the components of an exemplary data-processing system 1601 for analyzing data, operating an analyzer, and performing other analyses described herein, and related components. The system 1601 includes a processor 1686, a peripheral system 1620, a user interface system 1630, and a data storage system 1640. The peripheral system 1620, the user interface system 1630 and the data storage system 1640 are communicatively connected to the processor 1686. The processor 1686 can be communicatively connected to a network (not shown). The following devices can each include one or more of the systems 1686, 1620, 1630, 1640, and can each connect to one or more network(s): the controller 1186, the metering mechanism 1120, the incubator 1130, the light source 1142, the line-scan imager 1144 (all FIG. 11), and the metering mechanism 1220 (FIG. 12). The processor 1686, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

The processor 1686 can implement processes of various aspects described herein. The processor 1686 and related components can, e.g., carry out processes for performing assays or for enabling an assay device such as the assay device 100 to perform multiple tests based upon a single sample metering event. Examples of such processes are described above with reference to FIG. 13.

The processor 1686 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise.

The phrase "communicatively connected" includes any type of connection, wired or wireless, for communicating data between devices or processors. These devices or processors can be located in physical proximity or not. For example, subsystems such as the peripheral system 1620, the user interface system 1630, and the data storage system 1640 are shown separately from the data processing system 1686 but can be stored completely or partially within the data processing system 1686.

The peripheral system 1620 can include one or more devices configured to provide digital content records to the processor 1686. For example, the peripheral system 1620 can include or be communicatively connected with one or more measurement device(s) 1140, FIG. 11, to receive images such as those shown in FIGS. 14A and 15A, or other measurements of the assay device 100, FIG. 1, or other assay devices according to embodiments described herein. The processor 1686, upon receipt of digital content records (e.g., such images) from a device in or connected to the peripheral system 1620, can store such digital content records in the data storage system 1640. In various examples, the peripheral system 1620 is communicatively connected to the metering mechanism 1120, the incubator 1130, or the measurement device 1140, all FIG. 11, to permit the processor 1686 to control these devices via the peripheral system 1620. In various examples, the peripheral system 1620 (or the measurement system 1140, FIG. 11) includes at least one of the following devices configured to control, or receive data from, the measurement system 1140: an analog-to-digital (A/D) converter (ADC), a digital-to-analog (D/A) converter (DAC), a modem, a network interface (e.g., Ethernet or FIELDBUS), or a transceiver or transducer (e.g., an RS-422, LVDS, or 4-20 mA interface).

The user interface system 1630 can convey information in either direction, or in both directions, between a user 1638 and the processor 1686 or other components of the system 1601. The user interface system 1630 can include a mouse, a keyboard, another computer (connected, e.g., via a network or a null-modem cable), or any device or combination of devices from which data is input to the processor 1686. The user interface system 1630 also can include a display device, e.g., an electronic display 1635, a processor-accessible memory, or any device or combination of devices to which data is output by the processor 1686. The user interface system 1630 and the data storage system 1640 can share a processor-accessible memory.

The data storage system 1640 can include or be communicatively connected with one or more processor-accessible memories configured to store information. The memories can be, e.g., within a chassis or as parts of a distributed system. The phrase "processor-accessible memory" is intended to include any data storage device to or from which the processor 1686 can transfer data (using appropriate components of the peripheral system 1620), whether volatile or nonvolatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 1640 can be a tangible non-transitory computer-readable storage medium, i.e., a non-transitory device or article of manufacture that participates in storing instructions that can be provided to the processor 1686 for execution.

In an example, the data storage system 1640 includes a code memory 1641, e.g., a RAM, and a disk 1643, e.g., a tangible computer-readable rotational storage device such as a hard drive. Computer program instructions are read into the code memory 1641 from the disk 1643. The processor 1686 then executes one or more sequences of the computer program instructions loaded into the code memory 1641, as a result performing process steps described herein. In this way, the processor 1686 carries out a computer implemented process. For example, steps of methods described herein, blocks of the flowchart illustrations or block diagrams herein, and combinations of those, can be implemented by computer program instructions. The code memory 1641 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into the processor 1686 (and possibly also other processors), to cause functions, acts, or operational steps of various aspects herein to be performed by the processor 1686 (or other processor). Computer program code for carrying out operations for various aspects described herein may be written in any combination of one or more programming language(s), and can be loaded from the disk 1643 into the code memory 1641 for execution.

The invention is inclusive of combinations of the aspects described herein. References to "a particular aspect" (or "embodiment" or "version") and the like refer to features that are present in at least one aspect of the invention. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

PARTS LIST FOR FIGS. 1-16

100 assay device
101 fluidic sample
110 support
121, 122 test elements
130 diverter
131, 132 faces
140 common sample addition area
150 cover
155, 156 apertures 200 assay device
230 porous member
300 assay device
323, 324 test elements
330 diverter
331, 332, 333, 334 faces
335 apex
410 base
421, 422, 423 faces
424, 425 faces
430 diverter
435 apex
500 assay device
530 pyramidal diverter
550 fluid reservoir
600 assay device
601, 602 portions
621, 622 drop apertures
630 diverter
632 splitter
636 distance
700 assay device
707 microposts
730 diverter
735 substrate
741, 742, 743, 744 fluid flow paths
800 assay device
801 lateral-flow test element
802 sample receiving zone
803 reagent zone
804 detection zone
805 wicking zone
808 fluid flow path
809 substrate
891 lateral-flow test element
892 sample receiving zone
900 assay device
1000 assay device
1021-1028 test elements
1100 analyzer apparatus
1110 transport system
1120 metering mechanism
1121 piston
1122 driving system
1124 metering tip
1130 incubator
1140 measurement device
1142 light source
1144 line-scan imager
1186 controller
1200 assay device
1201, 1202 portions
1220 metering mechanism
1224 metering tip
1241, 1242 apertures
1250 cover
1255, 1256 apertures
1256 aperture
1310, 1320 steps
1330, 1340 steps
1350, 1352, 1355 steps
1421, 1422 test elements
1481, 1482 points
1492 line
1521, 1522 test elements
1581, 1582 points
1592 line
1601 data-processing system
1620 peripheral system
1630 user interface system
1635 electronic display
1638 user
1640 data storage system
1641 code memory
1643 disk
1686 processor

The invention claimed is:

1. An assay device comprising:
   a) a support;
   b) at least two test elements disposed at least partially over the support at least partly in proximity to each other to define a common sample addition area, wherein at least one of the at least two test elements is a dry slide analytical test element; and
   c) a diverter configured to divert a portion of a metered sample received at the common sample addition area onto each of the at least two test elements, wherein at least a portion of the at least two test elements is disposed between the support and the diverter.

2. The device as recited in claim 1, wherein at least one of the at least two test elements comprises a substrate having a plurality of projections outwardly extending from an upper surface of the substrate along a defined fluid flow path including a sample receiving zone in relation to the common sample addition area, wherein the projections have dimensions and a relative spacing between the projections that induce lateral capillary flow of a received sample.

3. The device as recited in claim 2, wherein at least one of the at least two test elements is a lateral-flow analytical test element.

4. The device as recited in claim 1, wherein the at least two test elements are in abutting relation.

5. The device as recited in claim 1, wherein the diverter further comprises a plurality of projections extending outward from the diverter, the projections having dimensions and relative spacing therebetween that induce lateral capillary flow of respective portions of the metered sample to the at least two test elements.

6. The device as recited in claim 1, further comprising a cover having an aperture operatively arranged with respect to the sample addition area to receive the metered sample.

7. The device as recited in claim 6, wherein the cover is substantially co-planar with the diverter.

8. The device as recited in claim 1, further including a fluid reservoir in the common sample addition area, the fluid reservoir being configured to receive the metered sample and convey at least part of the metered sample to the diverter.

9. The device as recited in claim 1, wherein the diverter consists of one or more material(s) that are substantially impermeable to the metered sample.

10. The device as recited in claim 1, wherein the diverter includes a substrate disposed at least partially in the common sample addition area, wherein the substrate is configured to conduct respective portions of the metered sample to the at least two test elements.

11. The device as recited in claim 10, wherein the diverter includes a plurality of projections extending outwardly from the substrate of the diverter, the projections having dimensions and spacing therebetween to induce lateral capillary flow of the respective portions of the metered sample to the at least two test elements.

12. The device as recited in claim 1, wherein the diverter has a polyhedral configuration including a plurality of faces disposed in relation to each of the at least two test elements and configured such that applied metered sample flows along a respective face to a corresponding test element.

13. The device as recited in claim 12, wherein the polyhedral configuration of the diverter comprises a pyramid configured so that the applied metered sample flowing along each face travels away from an apex of the pyramid.

14. The device as recited in claim 1, wherein the diverter comprises a porous member arranged at least partly over each of the at least two test elements, the porous member having a plurality of segments corresponding to the at least two test elements, wherein at least two of the segments have different cross-sectional areas.

15. The device as recited in claim 1, wherein the diverter is arranged over the at least two test elements and includes:
   a) a drop aperture for each of the at least two test elements; and
   b) a splitter configured to receive the metered sample and direct portions of the metered sample to each drop aperture.

16. The device as recited in claim 1, wherein the diverter comprises a porous member arranged at least partly over each of the at least two test elements, the device further including a blocking material substantially impermeable to the metered sample and arranged at least partly between the porous member and at least two test elements.

17. The device as recited in claim 16, wherein the blocking material is arranged to define gaps through which the provided portions of the metered sample from the splitter can pass from the diverter to drop apertures of the at least two test elements, and at least two of the gaps having different sizes.

18. The device as recited in claim 1, wherein the diverter comprises a porous member arranged at least partly over each of the at least two test elements, the porous member having a plurality of segments corresponding to respective apertures of the at least two test elements, wherein at least two of the segments have different cross-sectional areas.

* * * * *